(12) United States Patent
Mayer et al.

(10) Patent No.: US 12,272,440 B2
(45) Date of Patent: *Apr. 8, 2025

(54) METHODS, SYSTEMS, AND APPARATUS FOR OPTIMIZING EFFECTS OF TREATMENT WITH MEDICATION USING MEDICATION COMPLIANCE PATTERNS

(71) Applicant: I.D. THERAPEUTICS LLC, Madison, WI (US)

(72) Inventors: Steven L. Mayer, Salem, WI (US); David C. Kravitz, Barrington Hills, IL (US); Tracey H. Mayer, Salem, WI (US)

(73) Assignee: I.D. THERAPEUTICS LLC, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/588,928

(22) Filed: Feb. 27, 2024

(65) Prior Publication Data

US 2024/0249821 A1 Jul. 25, 2024

Related U.S. Application Data

(63) Continuation of application No. 16/166,601, filed on Oct. 22, 2018, now Pat. No. 11,942,209, which is a
(Continued)

(51) Int. Cl.
*G16H 20/10* (2018.01)
*G16H 20/13* (2018.01)
(Continued)

(52) U.S. Cl.
CPC ............. *G16H 20/70* (2018.01); *G16H 20/10* (2018.01); *G16H 20/13* (2018.01); *G16H 40/63* (2018.01);
(Continued)

(58) Field of Classification Search
CPC ........ G16H 20/70; G16H 40/67; G16H 20/10; G16H 40/63; G16H 20/13; G16Z 99/00; Y02A 90/10

See application file for complete search history.

(56) References Cited

U.S. PATENT DOCUMENTS

| 4,504,153 A | 3/1985 | Schollmeyer et al. |
| 4,939,705 A | 7/1990 | Hamilton et al. |
(Continued)

FOREIGN PATENT DOCUMENTS

| EP | 1 075 831 A1 | 2/2001 |
| NL | 1 010 391 C2 | 4/2000 |
(Continued)

OTHER PUBLICATIONS

Final Rejection Office Action issued in U.S. Appl. No. 12/888,133, filed Jul. 8, 2013, pp. 1-30 (Year: 2013).*
(Continued)

*Primary Examiner* — Kenneth Bartley
(74) *Attorney, Agent, or Firm* — Oliff PLC

(57) ABSTRACT

Methods, systems, and apparatus monitor medication usage data for one patient or a population of patients, which can be processed to determine compliance patterns. Such methods and systems can associate, analyze, organize and present medication usage data, compliance patterns, and correlations between compliance patterns and outcomes data for electronic analysis or analysis by a caretaker. Such methods, systems, and apparatus permit analysis of compliance patterns to enable, for example, establishment or adjustment of safe and effective treatment regimens, and may include feedback systems for ensuring authenticity of medication and/or effects of medication on a patient.

14 Claims, 6 Drawing Sheets

Related U.S. Application Data continuation of application No. 13/427,389, filed on Mar. 22, 2012, now abandoned, which is a continuation-in-part of application No. 12/888,133, filed on Sep. 22, 2010, now abandoned.

(51) Int. Cl.
  G16H 20/70 (2018.01)
  G16H 40/63 (2018.01)
  G16H 40/67 (2018.01)
  G16Z 99/00 (2019.01)

(52) U.S. Cl.
  CPC .............. G16H 40/67 (2018.01); G16Z 99/00 (2019.02); Y02A 90/10 (2018.01)

(56) References Cited

U.S. PATENT DOCUMENTS

| | | | |
|---|---|---|---|
| 5,239,491 | A | 8/1993 | Mucciacciaro |
| 5,408,443 | A | 4/1995 | Weinberger |
| 5,657,236 | A | 8/1997 | Conkright |
| 5,710,551 | A | 1/1998 | Ridgeway |
| 5,850,344 | A | 12/1998 | Conkright |
| 5,852,408 | A | 12/1998 | Christiansen et al. |
| 5,852,590 | A | 12/1998 | de la Huerga |
| 5,950,632 | A | 9/1999 | Reber et al. |
| 5,954,641 | A | 9/1999 | Kehr et al. |
| 5,971,594 | A | 10/1999 | Sahai et al. |
| 5,983,193 | A | 11/1999 | Heinonen et al. |
| 6,085,752 | A | 7/2000 | Kehr et al. |
| 6,102,855 | A | 8/2000 | Kehr et al. |
| 6,249,717 | B1 | 6/2001 | Nicholson et al. |
| 6,259,654 | B1 | 7/2001 | de la Huerga |
| 6,294,999 | B1 | 9/2001 | Yarin et al. |
| 6,380,858 | B1 | 4/2002 | Yarin et al. |
| 6,411,567 | B1 | 6/2002 | Niemiec et al. |
| 6,529,446 | B1* | 3/2003 | de la Huerga ........ A61J 7/0481 368/10 |
| 6,574,166 | B2 | 6/2003 | Niemiec |
| 6,604,650 | B2 | 8/2003 | Sagar |
| 6,751,730 | B1 | 6/2004 | Walker et al. |
| 6,961,285 | B2 | 11/2005 | Niemiec et al. |
| 7,002,476 | B2 | 2/2006 | Rapchak |
| 7,107,122 | B1 | 9/2006 | Whyte |
| 7,158,011 | B2 | 1/2007 | Brue |
| 7,269,476 | B2 | 9/2007 | Ratnakar |
| D552,739 | S | 10/2007 | Green |
| 7,295,890 | B2 | 11/2007 | Jean-Pierre |
| 7,304,913 | B2 | 12/2007 | Niemiec et al. |
| 7,545,257 | B2 | 6/2009 | Brue |
| 7,978,064 | B2 | 7/2011 | Zdeblick et al. |
| 2001/0028308 | A1 | 10/2001 | De La Huerga |
| 2001/0036664 | A1 | 11/2001 | Korngold et al. |
| 2002/0027507 | A1 | 3/2002 | Yarin et al. |
| 2002/0067270 | A1 | 6/2002 | Yarin et al. |
| 2002/0104848 | A1 | 8/2002 | Burrows et al. |
| 2002/0169635 | A1* | 11/2002 | Shillingburg .......... G16H 20/13 705/2 |
| 2002/0192159 | A1 | 12/2002 | Reitberg |
| 2003/0036683 | A1 | 2/2003 | Kehr et al. |
| 2003/0086338 | A1 | 5/2003 | Sastry et al. |
| 2003/0099158 | A1 | 5/2003 | De la Huerga |
| 2004/0133305 | A1 | 7/2004 | Jean-Pierre |
| 2005/0033133 | A1 | 2/2005 | Kraft |
| 2005/0182653 | A1 | 8/2005 | Urban et al. |
| 2006/0062734 | A1 | 3/2006 | Melker et al. |
| 2006/0124655 | A1 | 6/2006 | Ratnakar |
| 2006/0124656 | A1 | 6/2006 | Popovich |
| 2007/0016443 | A1 | 1/2007 | Wachman et al. |
| 2007/0039624 | A1 | 2/2007 | Roberts et al. |
| 2007/0073560 | A1 | 3/2007 | Walker et al. |
| 2007/0135691 | A1 | 6/2007 | Zingelewicz et al. |
| 2007/0156282 | A1 | 7/2007 | Dunn |
| 2007/0186923 | A1 | 8/2007 | Poutiatine et al. |
| 2007/0265880 | A1 | 11/2007 | Bartfeld et al. |
| 2008/0030309 | A1 | 2/2008 | Darrouzet |
| 2008/0054007 | A1 | 3/2008 | Mador |
| 2008/0059228 | A1 | 3/2008 | Bossi et al. |
| 2008/0090879 | A1 | 4/2008 | Friedman et al. |
| 2008/0099367 | A1 | 5/2008 | Niemiec et al. |
| 2008/0114490 | A1 | 5/2008 | Jean-Pierre |
| 2008/0195414 | A1 | 8/2008 | Duckert |
| 2008/0201168 | A1 | 8/2008 | Brown |
| 2008/0213904 | A1 | 9/2008 | Sliwa et al. |
| 2008/0281630 | A1 | 11/2008 | Sekura |
| 2009/0075274 | A1 | 3/2009 | Slepnev et al. |
| 2009/0134181 | A1 | 5/2009 | Wachman et al. |
| 2009/0187167 | A1 | 7/2009 | Sexton et al. |
| 2009/0192648 | A1 | 7/2009 | Namineni et al. |
| 2010/0105717 | A1 | 4/2010 | Gordon et al. |
| 2012/0016690 | A1 | 1/2012 | Ramarajan et al. |
| 2012/0072231 | A1 | 3/2012 | Mayer et al. |

FOREIGN PATENT DOCUMENTS

| | | |
|---|---|---|
| WO | 98/38909 A1 | 9/1998 |
| WO | 2006/035278 A1 | 4/2006 |
| WO | 2008/064134 A2 | 5/2008 |
| WO | 2008/079340 A2 | 7/2008 |
| WO | 2011/112606 A1 | 9/2011 |
| WO | 2012/013723 A1 | 2/2012 |

OTHER PUBLICATIONS

Sep. 23, 2014 International Preliminary Report on Patentability issued in International Patent Application No. PCT/US2013/033523.

Dolan, "Proteus receives patent for ingestible sensor", Jul. 14, 2011, http://mobihealthnews.coml11923/proteus-receives -patent-for-ingestible-sensor, pp. 1-6.

Nov. 18, 2013 International Search Report and Written Opinion issued in International Patent Application No. PCT/US2013/033523.

Vrijens, Bernard et al., "Successful Projection of the Time Course of Drug Concentration in Plasma During a I-Year Period from Electronically Compiled Dosing-Time Data Used as Input to Individually Parameterized Phannacokinetic Models," Journal of Clinical Pharmacology, 2005, 45:1-000, pp. 1-7.

"The SIMpill Medication Adherence Solution," 2008, pp. 1, http://www.simpill.comlthesimplesolution.html.

"How the SIMpill Medication Adherence Solution Works," 2008, pp. 1-2, http://www.simpill.com/howsimpillworks.html.

"Products-On-Cue Compliance Service," 2006, pp. 1-2, http://www.simpill.com/p-occs-main.html.

Prendergast, Mary B. et al., "Optimizing Medication Adherence: An Ongoing Opportunity To Improve Outcomes After Kidney Transplantation," Clin J Am Soc Nephrol, vol. 5, pp. 1305 1311, 2010.

Chavers, Blanche M. et at, "Infection-Related Hospitalization Rates in Pediatric versus Adult Patients with End-Stage Renal Disease in the United States," Clin J Am Soc Nephrol, vol. 18, pp. 952-959, 2007.

Nevins, Thomas E. et al., "Quantitative Patterns of Azathioprine Adherence After Renal Transplantation," Clinical and Translational Research, vol. 87(5), pp. 711-718, Mar. 15, 2009.

Fredericks, Emily M. et al., "Adherence to immunosuppressants: how can it be improved in adolescent organ transplant recipients?," Pediatric Transplantation, vol. 15, issue 5, pp. 614-620, Oct. 2010.

Cravedi, Paolo et al., "Noninvasive Methods to Assess the Risk of Kidney Transplant Rejection," Expert Review of Clinical Immunology, vol. 5(5), pp. 535-546, 2009.

Schafer-Keller, P. et al., "Non-Adherence measurement in kidney transplantation," American Journal of Transplantation, vol. 8(3), pp. 616-626, 2008.

Denhatirynck, K. et al., "Prevalence and risk factors of non-adherence with immunosuppressive medication in kidney transplant patients," American Journal of Transplantation, vol. 7, pp. 108-116, 2007.

(56) References Cited

OTHER PUBLICATIONS

Vrijens, Bernard et al., "Adherence to Prescribed Antihypertensive Drug Treatments: Longitudinal Study of Electronically Compiled Dosing Histories," BMJ, published online May 14, 2008; doi: 10.1136/bmj.39553.670231.25.
Feb. 22, 2012 Invitation to Pay Additional Fees and Partial International Search Report issued in International Patent Application No. PCT/US2011/052522.
Jan. 28, 2013 Office Action Issued in U.S. Appl. No. 12/888,133.
"A&D Medical Wireless Activity Monitor with Software (AEXL20)," retrieved Mar. 13, 2012, http://www.restockit.com/wireless-activity-monitor-with-software(aex120).html?source=IDx20111014x00001a&utm_source=IDx20111014x00001a&utm_medium=free&utm_campaign=comparison&utm_term=AEXL20&bvar7=google&bvar10=google&ci_src= 14110944&ci_sku=AEXL20.
Olsen, S., "Cell phones to measure blood sugar levels?," CNET News, Jun. 18, 2008, retrieved Mar. 13, 2012, http://news.cnet.coml8301-10784_3-9971871-7.html.
"iHealth HS3 Wireless Bluetooth Scale for IOS," retrieved Mar. 13, 2012, http://www.google.com/products/catalog?hl=en&client=safari&rls=en&q=weight+scales+wireless&bav=on.2,or.r~ccpw .cqf.,cf.osb&bi w=1345&bih=670&um=l&ie=UTF-8&tbm=shop&cid=6392145607960782090&sa=X&ei=UOdfT9iuD4K4OgHMqcnHBw&ved=OCIUBEPMCMAI#ps-sellers.
"Tanita HD-351ANTTM Digital Weight Scale," retrieved Mar. 13, 2012, http://www.google.comlproducts/catalog?hl=en&client=safari&rls=en&q=weight+scales+wireless&bav=on.2,or.r~c_pw.cqf.,cf.osb&biw=1345&bih=670&um=l&ie=UTF-8&tbm=shop&cid=10568498244606457076&sa=X&ei=UOdfT9iuD4K40gHMqcnHBw&ved=OCIKBEPMCMAM#ps-sellers.
"LifeSource UA-767PBT Blood Pressure Monitor—Wireless Bluetooth," retrieved Mar. 13, 2012, http://www.google.comlproducts/catalog?hl=en&q=blood+pressure+monitor+wireless&bav=on.2,or.r~c.cpw.r_qf.,cf.osb&biw=1345&bih=670&um=l&ie=UTF-8&tbm=shop&cid=7643227785268489072&sa=X&ei=ckhfT_-FGPiOQGOx8CsBw&ved=OCGQQ8w 1 w AA#ps-sellers.
"LifeSource LifeSource Ua-851ant eHealth Wireless Multi-Function Auto Blood Pressure Monitor," retrieved Mar. 13, 2012, http://www.google.com/products/catalog?hl=en&q=blood+pressure+monitor+wireless&bav=on.2,or.r~gc.cpw.cqf.,cf.osb&biw=1345&bih=670&um=l&ie=UTF-8&tom=shop&cid= 15882907778294813809&sa=X&ei=ckhfL -FGPiOQGOx8CsBw&ved=OCG4Q8wlwAg#ps-sellers.
Jul. 28, 2014 Office Action issued in U.S. Appl. No. 13/427,389.
Dec. 19, 2014 Office Action issued in U.S. Appl. No. 13/427,389.
Jan. 14, 2016 Office Action Issued in U.S. Appl. No. 13/427,389.
Jul. 27, 2016 Office Action issued in U.S. Appl. No. 13/427,389.
Dec. 13, 2016 Advisory Action issued in U.S. Appl. No. 13/427,389.
Sep. 20, 2017 Office Action Issued in U.S. Appl. No. 13/427,389.
Jul. 8, 2013 Office Action issued in U.S. Appl. No. 12/888,133.
Apr. 27, 2012 International Search Report Issued in International Patent Application No. PCT/US2011/052522.
Apr. 27, 2012 Written Opinion of the International Search Authority issued in International Patent Application No. PCT/ US2011/052522.
Frassetto, Lynda, et al. "Cyclosporine pharmacokinetics and dosing modifications in human immunodeficiency virus-infected liver and kidney transplant recipients." Transplantation 80.1 (2005): 13-17. (Year: 2005).
Kim, Jerome H ., and John R. Perfect. "Infection and cyclosporine." Reviews of infectious diseases 11.5 (1989): 677-690. (Year: 1989).
Sommerer, Claudia, et al. "Pharmacodynamic monitoring of cyclosporine a in renal allograft recipients shows a quantitative relationship between immunosuppression and the occurrence of recurrent infections and malignancies." Transplantation 82.10 (2006): 1280-1285. (Year: 2006).
Preiksaitis, Jutta K., et al. "Infections due to herpesviruses in cardiac transplant recipients: role of the donor heart and immunosuppressive therapy." Journal of Infectious Diseases 147 .6 (1983): 97 4-981. (Year: 1983).
Funk, Georg A., Jurg Steiger, and Hans H. Hirsch. "Rapid dynamics of polyomavirus type BK in renal transplant recipients." The Journal of infectious diseases 193.1 (2006): 80-87. (Year: 2006).
Hernández, Gonzalo, et al. "Reduction of severe gingival overgrowth in a kidney transplant patient by replacing cyclosporin A with tacrolimus." Journal of periodontology 71.10 (2000): 1630-1636. (Year: 2000).

* cited by examiner

METHODS, SYSTEMS, AND APPARATUS FOR OPTIMIZING EFFECTS OF TREATMENT WITH MEDICATION USING MEDICATION COMPLIANCE PATTERNS

This application is a Continuation of U.S. patent application Ser. No. 16/166,601, filed Oct. 22, 2018, which in turn is a Continuation of U.S. patent application Ser. No. 13/427,389, filed Mar. 22, 2012, which is a Continuation-in-Part of U.S. patent application Ser. No. 12/888,133, filed Sep. 22, 2010. The disclosures of the prior applications are incorporated herein by reference in their entirety.

FIELD OF INVENTION

The disclosure relates to methods, systems, and apparatus for monitoring patient medication usage, determining medication compliance patterns, and establishing and adjusting medication regimens. The disclosure further relates to methods, systems, and apparatus for monitoring, storing, and analyzing patient medication usage data and compliance patterns, associating the compliance patterns with medication properties data and patient history data, and determining a correlation between medication compliance patterns and the other data.

BACKGROUND

Medications may include potent chemical and/or biological elements designed to induce a specific ameliorative effect on a patient's disease state or medical condition. Medication manufacturers, prescribing physicians, and caretakers have limited information about a given medication that typically includes only basic guidelines for safely and effectively prescribing very powerful substances to patients.

This dearth of information is especially significant with regard to the effects of medication treatment regimen compliance. Medication manufacturers, prescribing physicians and other caretakers struggle to effectively manage the effects on patients of non-compliant medication intake or compliance patterns. For example, without data regarding patient medication usage, caregivers face difficulty discerning whether negative effects of medication intake are the result of precise, over, or under compliance by the patient, or a prescribed treatment regimen that is ineffective or unsafe. There are few or no independent objective measures of a patient's actual compliance with a prescribed treatment regimen, aside from the patients' memory about their own historical medication compliance over time. Further, there are few or no independent objective measures of negative or ameliorative effects attributable to varying degrees of over and/or under compliance with treatment regimens.

Poor or unexpected medication treatment regimen compliance is a medical problem that poses risks to patient health and potentially increases health care costs. By way of example, a patient who has undergone an organ transplant may be prescribed a regimen of immunosuppressive medications to protect the patient's transplanted organ from being rejected by the patient's immune system. If a patient takes too much or too little of these medications, or takes them at incorrect time intervals, then the patient's body may experience a cascade of biochemical reactions that may result in the transplanted organ being rejected or other diseases being acquired, or other complications.

For example, if a patient takes too much of an immunosuppressive medication, even intermittently, the patient's inherent immunological capability may be adversely affected, thereby rendering the patient susceptible to malignancies, bacterial infections and viral infections. The complications of an over-suppressed immune system can lead to death, severe illness that requires hospitalization, and can compromise the transplanted organ. The medical intervention often expended to redress such adverse consequences can add significant direct and indirect financial costs for the patient and the health care system, in addition to potentially limiting the patient's quality of life.

SUMMARY

Methods, systems, and apparatus are needed that provide robust checks and balances for establishing medication regimens, adjusting medication regimens, and caring for patients who are taking medications. Further, methods, systems, and apparatus are needed that permit monitoring, analysis, and recording of medication usage data and regimen compliance patterns for individual patients and patient populations. Further still, methods and systems are needed that permit analysis of medication regimen compliance patterns in view of patient history data to enable, for example, medication manufacturers and/or prescribing caretakers to safely and efficaciously establish and adjust treatment regimens.

Embodiments of methods, systems, and apparatus described herein fulfill needs for readily accessible data concerning medication regimen compliance and patient history data, for individual patients or populations of patients. Methods, systems, and apparatus provide access to medication usage data and compliance patterns. Methods, systems, and apparatus permit analysis of associated medication compliance patterns, outcomes data, medicine interaction data, biomarker data and establishment and adjustment of medication dosage regimens.

For example, embodiments of methods permit optimizing effects of treatment with medication by establishing medication regimens based on medication compliance patterns. The medication compliance patterns are determined by performing statistical analysis on medication usage data using a processor.

Embodiments include systems for optimizing the effects of treatment with medication that may have a medication monitor, a receiving system, and a compliance data processor that processes medication usage data to produce one or more medication compliance pattern. Embodiments include systems that may have a storage system for storing at least one of medication compliance pattern, medication properties data, outcomes data, biomarker data, and patient history data. The systems may include a treatment regimen processor that establishes a treatment regimen based on at least one of the medication compliance pattern, medication properties data, outcomes data, biomarker data, a pre-established treatment regimen, and patient history data. The systems may include a biomarker device that is configured to output the biomarker data to the treatment regimen processor or some other device.

Embodiments include a monitor that may include a housing body defining an opening that accommodates insertion and removal of medication that may be contained by the monitor. The housing body may include a plurality of housings each configured to accommodate a specific shape of a pre-filled medication insert. The monitor may include a lid that slideably covers and uncovers the opening, and a sensor for determining when the opening is uncovered. The monitor may be equipped with a processor for determining medication compliance patterns based on medication usage data sensed by the monitor by way of, for example, sensing the covering and uncovering of the opening by the lid. The monitor may include a sensor to detect, for example, an origin of manufacture of the pre-filled medication insert. Each pre-filled medication insert may have a barcode, RFID tag or other identifier that relays the origin of manufacture data and other data to verify authenticity of the medication. The monitor may include a reader such as a barcode reader, an RFID label reader or other information detector that verifies that the medication is not counterfeit at the time the monitor is loaded and/or at the time of use by the patient. The RFID information may also be sent to a receiving system such as a remote server, which verifies, and may send a signal to the monitor and/or another receiver, regarding whether the medication is authentic. The monitor may also or instead include a sensor to detect a specific shape of a medication, the specific shape of the pre-filled medication insert, a medication made by a unique manufacturing process, or an orientation of the medication within the housing body.

Embodiments include methods that may accommodate optimizing treatment of a transplant recipient. Methods may include providing a patient with a medication monitor that can provide usage data regarding the patient's compliance with an immunosuppressant treatment regimen. Methods may include collecting the usage data at a central server over a predetermined period of time, and determining over the predetermined period of time a patient's compliance pattern with the treatment regimen. Further, methods may include obtaining a diagnostic test or biomarker result indicative of a level of immunosuppression of the patient, comparing the patient's compliance pattern with the diagnostic results, and, based on the comparison, outputting a recommendation of replacing an immunosuppressant medication used in the treatment with a different medication, changing a dosage amount and/or frequency of an immunosuppressant medication, or not changing the regimen.

Exemplary embodiments are described herein. It is envisioned, however, that any system that incorporates features of methods, systems, and apparatus described herein are encompassed by the scope and spirit of the exemplary embodiments.

DETAILED DESCRIPTION OF EMBODIMENTS

Figure 1:
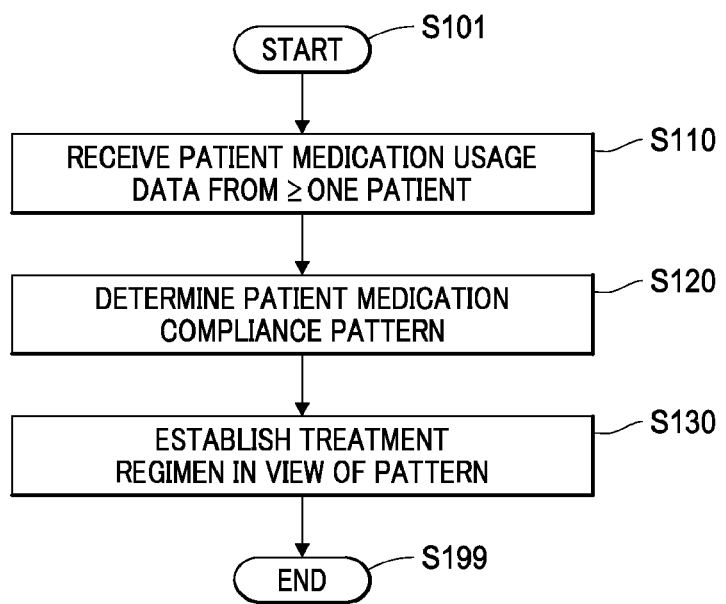
FIG. 1 is a flow diagram of a method of establishing a treatment regimen in accordance with an exemplary embodiment.

Exemplary embodiments are intended to cover all alternatives, modifications, and equivalents as may be included within the spirit and scope of the methods, systems, and apparatus as described herein.

Reference is made to the drawings to accommodate understanding of methods, systems, and apparatus for medication usage and treatment regimen compliance monitoring and informed treatment regimen establishment, including adjustment or optimization. In the drawings, like reference numerals are used throughout to designate similar or identical elements. The drawings depict various embodiments and data related to embodiments of illustrative methods, systems, and apparatus incorporating features of exemplary embodiments described herein.

Embodiments include one or more medication monitors having a housing and/or container for holding one or more types of medication for one or more patients. A monitor may include a sensor for sensing medication usage data such as a time, a date, a location of medication insertion, usage, dispensing, consumption, or the like. The monitor may include one or more sensors for sensing patient medication usage by way of, for example, sensing the position of a lid that covers or uncovers a cavity, housing, cartridge, chamber, or other opening, closing, filling, refilling, or dispensing structure. The monitor may include a processor that enables the apparatus to monitor, record, and generate, for example, medication usage data such as time, date, and/or location of medication consumption. The location of medication consumption may determined with a medication monitor that is equipped with, for example, global positioning satellite technology ("GPS") and/or wireless communication technology such as cell phone technology. Further the processor may enable the apparatus to monitor and record usage data such as the amount of medication remaining in one or more containers. The monitor may be constructed to accept, contain, and dispense one or more medications by containing medications separately, in prescription pharmacy containers, bottles, blisterpacks, and/or by way of cartridges or chambers. The monitor may include a display, and may be constructed to dispense contained medication. The identity of one or more medications may be determined with a medication monitor that is equipped with, for example, an RFID sensor.

In embodiments, a medication monitor may include a compliance pattern processor that determines compliance patterns based on statistical analysis or other now known or later developed systems. The medication monitor may include a treatment regimen processor that determines a treatment regimen based on the compliance pattern. The medication monitor may include a processor that provides an output that suggests alternatives in view of medication compliance patterns, medication properties data, outcomes data, biomarker data, and/or patient history data. In embodiments, such processors may be in separate apparatus (e.g., in one or more remote servers).

The medication monitor may be constructed to communicate with one or more receiving systems, such as a remote computer, another medication monitor, a cellular or landline telephone, or other receiving or remote communications device, for example of a patient, central repository, server, healthcare facility, caretaker, or family member. For example, the medication monitor may be constructed to include a port for connecting and communicating with a separate receiving system by way of a universal serial bus connection or a cable connection. The medication monitor may include a transmitter for communicating wirelessly. The medication monitor may be located on the same network as a receiving system, or on a different network. The medication monitor may communicate data to a receiving system for presentation or storage. The receiving system may communicate with, or may include, a storage system for storing the medical usage data, compliance pattern, or regimen data. Further, the receiving system may include a computer program for analyzing and organizing the usage data or compliance pattern, and for formatting the information for presentation to a patient, health care provider, medication researcher, developer or manufacturer, or other interested party (hereafter "interested party").

The receiving system may not be limited to merely receiving data from the medication monitor, but may also transmit signals and data to the medication monitor. For example, the receiving device may request that the medication monitor send data, or may transmit data to the monitor such as software updates, new software, or new adjusted dosage regimens. Information such as new adjusted dosage regimens, a time, an amount of remaining medication, a reminder, and/or a warning may be communicated to a patient by way of a display located on or in communication with the monitor. Other messages, for example messages targeted to specific patients or populations of patients, could be disseminated though the monitor. For example, monitors associated with a certain medication can be targeted with information or inquiries about that medication (e.g., recall notices or commercial or educational information) or generally about the type of medication or related health conditions. Because of the transmission capability of the monitor, such features could be used for two-way communications such as surveys. This capability may preferably be associated with a switch or programming choice to enable or disable such communications, particularly incoming commercial information.

The receiving system may be in communication with one or more medication monitors. For example, the receiving system may communicate with a gateway of a network of medication monitors. The network may be a wide area network or a local area network. The networks may be of any topology now known or later developed, including tree, mesh, or star. The networks may be peer-to-peer or server/client. The receiving system may be located on the same network as or a different network from the one or more medication monitors. The receiving system may receive and/or communicate with medication monitors on more than one network.

The receiving system may also be configured to receive patient history data that includes, for example, a historical record of deleterious and/or ameliorative effects of a medication on a patient or population of patients, optionally correlated to particular patient medication usage compliance patterns. The receiving system may also be configured to receive medication properties data related to, for example, the effects of an interaction between a prescribed medication and another medication.

The receiving system may be a remote server. The receiving system may be configured to store and present received data upon demand from an interested party using a storage system and/or a reporting system. In this manner, the receiving system may function to communicate warnings based on an analysis of monitored patient medication usage data, medication compliance patterns, and medication interaction data. Further, the receiving system may be configured with a computer program for analyzing the patient medication compliance pattern, outcomes data, and medication interaction data to organize the data for presentation, and/or to determine a correlation therebetween. Still further, the receiving device may be configured with a computer program for analyzing a correlation between the patient medication compliance pattern and the outcomes data in view of a treatment regimen, and that outputs one or more predictions pertaining to the effects on the patient of the treatment regimen, or the effects of potential treatment regimens, and present the output. The receiving device may include a computer program for ranking the data, or otherwise assigning values to highlight particular aspects of the data for presentation to an interested party.

Embodiments include methods for monitoring patient medication usage and generating corresponding compliance patterns for at least one patient. For example, embodiments include methods for monitoring patient medication usage and generating compliance patterns for one or more population of patients. Exemplary populations of patients could be defined, for example, based on treatment-related or treatment-unrelated characteristics. For example, certain populations may be determined to share compliance characteristics—e.g., populations above or below a certain age or suffering from certain conditions (e.g., Alzheimers), may be more forgetful; populations with certain lifestyle attributes (e.g., alcoholics, drug addicts) may be less rigorous, more forgetful and/or more oppositional to treatment; gender-based populations may have different compliance characteristics with respect to certain types of medications (e.g., contraceptives, erectile dysfunction medications) than with respect to other types of medications (e.g., blood pressure control medications).

Further, the usage data and compliance patterns may relate to more than one monitored medication. The monitoring may be, hut does not have to be, accomplished by using a medication monitor as described herein. Embodiments include using a medication monitor for monitoring at least one of a time, a date, and a location of medication usage. Also, embodiments include monitoring the time and/or date that a dosage of medication is removed from a monitored medication container. A method for patient medication usage monitoring may include transmitting medication usage data to a remote monitoring server, receiving the usage data, and storing the medication usage data and/or compliance pattern, whether on the server, or on another device that is in communication with the medication monitor and/or system.

Embodiments include methods, systems, and apparatus wherein medication usage data may be used to determine a medication compliance pattern for the one or more patients to which the usage data pertains or for other patients. Medication compliance patterns may be stored, whether on the receiving device or on another device in communication with the medication container monitoring apparatus and/or system. The medication usage data and/or medication compliance patterns may be organized for presentation to any interested parties. As used herein, a compliance pattern is a statistical pattern derived from a plurality of data points of medication usage data gathered over a period of time, such as not less than one week, four weeks, three months, six months or a year or more. The pattern could reflect, for example, percentage of doses missed, taken early (optionally including an indication of how early), taken late (optionally including an indication of how late), or taken on time.

Embodiments include methods for establishing a medication dosage regimen including receiving medication usage data from one or more patients using one or more patient medication monitor. Methods include determining a medication compliance pattern based on the received usage data, wherein the compliance pattern relates to a pre-established treatment regimen. Embodiments include methods for adjusting a pre-established treatment regimen or establishing an entirely new (i.e., initial) treatment regimen based on patient medication compliance patterns.

In embodiments, methods include receiving medication properties and/or patient history data pertaining to the positive and/or negative effects of a medication on a patient's health. This data may be received from a patient, a health care provider, a drug developer/manufacturer, a private database, and/or a central repository. Methods may further include receiving medication interaction data regarding the effects of interactions between the medication and other medications that a patient has taken or is taking. The medication interaction data may relate to one patient or a population of patients. The medication interaction data may be analyzed with patient medication usage data or a medication compliance pattern determined based on the patient medication usage data. The data may be stored, and may be organized for presentation to an interested party.

FIG. 1 shows methods involving medication usage monitoring, and determining a medication compliance pattern in accordance with an exemplary embodiment. The methods may be carried out using a medication monitor and treatment optimization system as described herein. At S101, a patient may be given a medication and a treatment regimen associated therewith that the patient is instructed to follow. The patient's usage of the medication is monitored to generate patient medication usage data. The patient medication usage data may be received at S110 at or from, for example, a medication monitor as described herein. The medication monitor may be constructed to contain a single medication or multiple medications. The patient medication usage data may relate to the single medication or the multiple medications. The patient medication usage data may relate to a single patient, or the patient medication usage data may relate to a population of patients. The usage data may concern the doses of one or more medications in a container, and may concern the time, date, and/or location at which medication is added to or removed from the container. The usage data may be based on the patient taking active medication or a placebo administered to establish a compliance pattern before active medication is administered or to help determine what, if any, active medication(s) may safely and/or effectively (and/or cost-effectively) be administered. As used herein, the term "medication" may include a placebo unless otherwise indicated by the context.

The patient medication usage data may be analyzed to determine a patient medication compliance pattern as shown at S120 of FIG. 1. The patient medication compliance pattern may be determined by way of a processor, using, for example, a computer-run algorithm that causes the processor to execute statistical analysis of the usage data. Alternatively, the usage data may be organized for presentation in a manner that accommodates determining a patient medication compliance pattern by way of, for example, graphical, diagrammatical or other representations of the usage data. For example, the patient medication usage data may be sensed by a medication monitoring apparatus, which may communicate the usage data to a receiving system, such as a remote monitoring server that is connected to a display. The receiving system may analyze the usage data, and organize the data in a presentation format for display to an interested party. The interested party may rely on the display of organized patient medication usage data to understand actual patient compliance patterns and associate them with patient history data, including outcomes data associated with the compliance patterns, for informed treatment regimen establishment and adjustment, and compliance monitoring.

Compliance patterns may be determined based on patient medication usage data from a patient who, for example, is pre-therapy, wherein the medication is a placebo. Further, compliance patterns may be determined based on patient usage data from a patient who is pre-therapy, wherein an active medication has been previously prescribed. Compliance patterns may also be determined based on patient medication usage data from a patient who is undergoing therapy and has been prescribed medications. Compliance patterns may be used to establish a treatment regimen, or for other purposes, such as for input to a compliance incentive program. For example, external rewards such as money, food, discounts, services, etc. may be provided to a patient or population of patients based on their compliance patterns. These rewards may be used as incentives to promote compliance, and/or to reflect the effects of different levels of compliance. For example, insurance premiums can be adjusted based on compliance patterns, as an incentive and/or as a financial protection for the insurance provider. Notifications can be provided to incentive program staff, patients and other interested parties to provide positive or negative feedback when compliance patterns are improving, maintaining or deteriorating.

At S130, FIG. 1 shows a step of establishing a treatment regimen. The treatment regimen may be a standardized treatment regimen or an individual patient treatment regimen. A treatment regimen may be established in view of the patient medication compliance pattern determined at S120. The treatment regimen may be established so as to maximize efficacy and safety, which may be determined in part by way of the patient medication compliance pattern. For example, the determined medication compliance pattern may be correlated with health variables of the monitored patient to predict the effects of medication intake, and to enable a caretaker to actively monitor and adjust an individual patient's medication intake by changing a dosing frequency and/or dosage amount. Health variables may include individual patient data such as physical or physiological data regarding weight, body mass index, gender, and data related to other medications or other substances (e.g., alcohol, tobacco) that the patient is taking or has taken. The determined medication compliance pattern may be analyzed in view of medication properties such as toxicity levels, and half-life of a particular medication.

Various algorithm techniques may be employed for analyzing the patient medication compliance pattern, and for correlating the pattern with health variables. Exemplary techniques include traditional statistical methods, multiple linear regression models, simple mixed logistic regression analysis, generalized linear mixed effects models, marginal models and generalized estimating equations, models for longitudinal data analysis, support vector machines, neural networks, K-nearest neighbor interpolation, non-linear methods, and other methods.

The algorithms may effect, in part, the step of establishing a treatment regimen at S130, and/or the step of determining a medication compliance pattern at S120. Further the algorithms may provide a result at S199 of providing warnings or messages to interested parties such as patients, family, caretakers, and support organizations. The algorithms may output status reports to patients and health care providers, or result in the change or establishment of a treatment regimen, whether by frequency of dosing or dosage amount, or the type and/or number of medications and/or other treatments prescribed. Further, the algorithms may output orders for specific tests or measures, or data upon which decisions to request such orders may be based.

Figure 2:
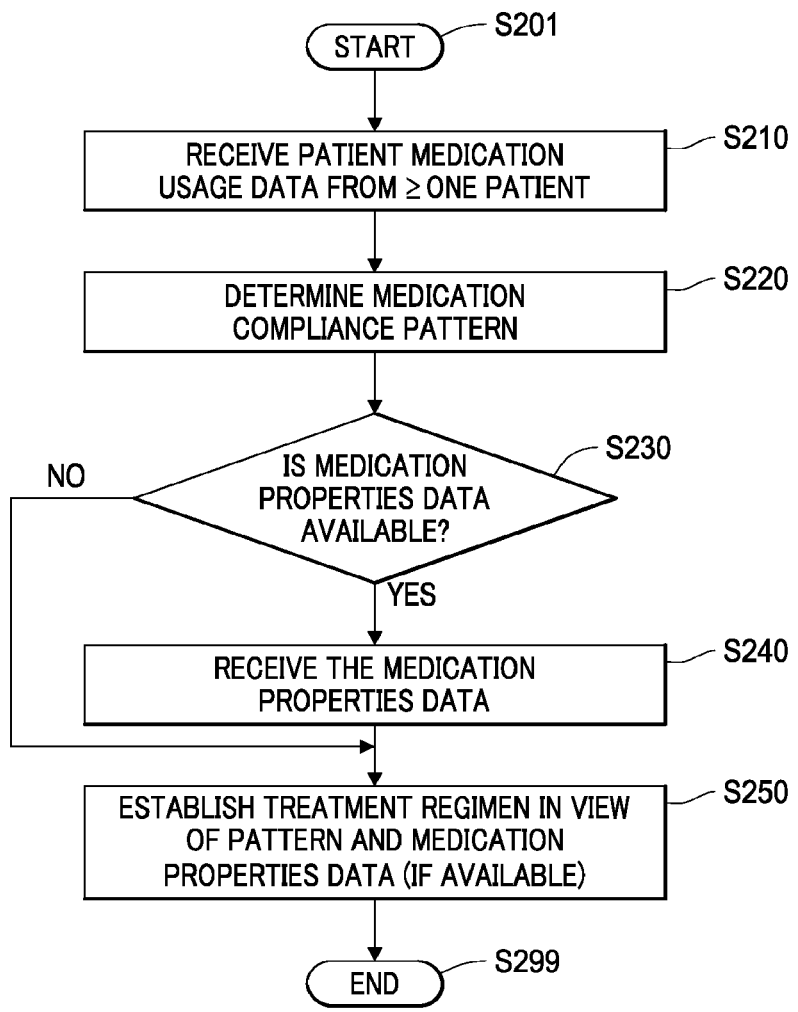
FIG. 2 is a flow diagram of a method of establishing a treatment regimen in accordance with an exemplary embodiment.

FIG. 2 shows a method of establishing a treatment regimen in accordance with an exemplary embodiment. The method may be carried out using a medication monitor and/or medication usage monitoring system as described herein. At S201, a patient may be given a medication and a dosing regimen associated therewith that the patient is instructed to follow, and with which the patient may use a medication monitor to monitor the patient's usage of the medication and to generate patient medication usage data. The patient medication usage data may be received at S210 at or from a medication monitor as, for example, described herein. The medication monitor may hold a single medication, or may be constructed to hold multiple medications. In embodiments, the patient medication usage data may relate to the single medication or the multiple medications. In embodiments, the patient medication usage data may relate to a single patient, or the patient medication usage data may relate to a population of patients. The usage data may concern the number of doses in a monitor at a given time, and may concern a time, a date, and/or a location at which a medication is dispensed, added to, or removed from the monitor.

The patient medication usage data may be analyzed to determine a medication compliance pattern as shown at S220 of FIG. 2. The medication compliance pattern may be determined by way of a processor, using, for example, a computer-run algorithm. Alternatively, the patient medication usage data may be organized and formatted for presentation in a manner that accommodates determining a patient medication compliance pattern by way of, for example, graphical and/or diagrammatical representations of patient medication usage data. For example, the patient medication usage data may be sensed and communicated by a medication monitor, which may communicate usage data to a receiving system or storage system, such as a remote monitoring server that is connected to a display. The remote server may analyze the usage data, and organize the data for display to an interested party, for example, a health care provider. The health care provider may rely on the display of organized patient medication usage data to determine a compliance pattern(s). The analysis may take into account patient travel and time zone changes, for example by basing the analysis on options of keeping the same dosing time as in an original time zone or adjusting the dosing time to the new time zone.

At S230, a determination may be made as to the availability of medication properties data. Medication properties data may include measures of safety and/or efficacy. Such measures may take into account, for example, such information relating to ongoing treatment regimens or "take-as-needed" (e.g., "PRN") regimens. For example, a take-as-needed regimen compliance pattern may particularly address toxicity issues such as overdosing patterns. The medication properties data may include recorded side effects, and recorded ameliorative and/or deleterious effects of medication usage on a patient or population of patients. Medication properties data may also include medication interactions data and/or biomarker data. If medication properties data are available, the data are received at S240. The medication properties data may be received from a repository or database of medication properties data.

At S250, FIG. 2 shows a method of establishing a treatment regimen. A treatment regimen may be established in view of the determined patient medication compliance pattern. The treatment regimen may be established so as to maximize efficacy and safety, which may be determined by way of the patient medication compliance pattern and medication properties data. The treatment regimen may also be established in view of patient history data. For example, the determined medication compliance pattern may be correlated with a health status of the monitored patient, and/or outcomes data, to predict the effects of medication intake, and to enable a caretaker to actively monitor and adjust an individual patient's medication intake by changing a dosing frequency and/or dosage amount. The outcomes data may include data output by a biomarker device (described below) that may be implanted in the patient and/or provided external to the patient.

Various algorithm techniques may be employed for analyzing the patient medication compliance pattern data, medication properties data, and patient history data. Exemplary techniques include traditional statistical methods, multiple linear regression models, simple mixed logistic regression analysis, multiple regression analysis, Quadratic Discriminant Analysis, Classification and Regression Trees, generalized linear mixed effects models, marginal models and generalized estimating equations, Analysis of Variance (ANOVA), Analysis of Co-Variance (ANCOVA) models for longitudinal data analysis, Principle Component Analysis (PCA), Linear Discriminant Analysis (LDA), support vector machines, neural networks, K-nearest neighbor interpolation, non-linear methods, and other methods. Analysis may be undertaken using software including but not limited to: SAS Version 8.02 or more recent version, ViSta (The Visual Statistics System), MATLAB, S+, STATA, MATLAB SVM, RapidMiner, Shogun, ACMB, Chronux, OpenEpi, SPSS, PSPP, SciPy, CRM114, and other software.

The algorithms may effect in part the step of establishing a treatment regimen at S250, and/or the step of determining a medication compliance pattern at S220. Further the algorithms may provide a result at S299 of providing warnings, messages, treatment options, or adjusted regimens to interested parties. The algorithms may output status reports to interested parties, or result in the change of a dosage regimen, whether in frequency or amount of dosage, or the type and/or number of medications prescribed. Further, the algorithms may output orders for specific tests or measures.

Figure 3:
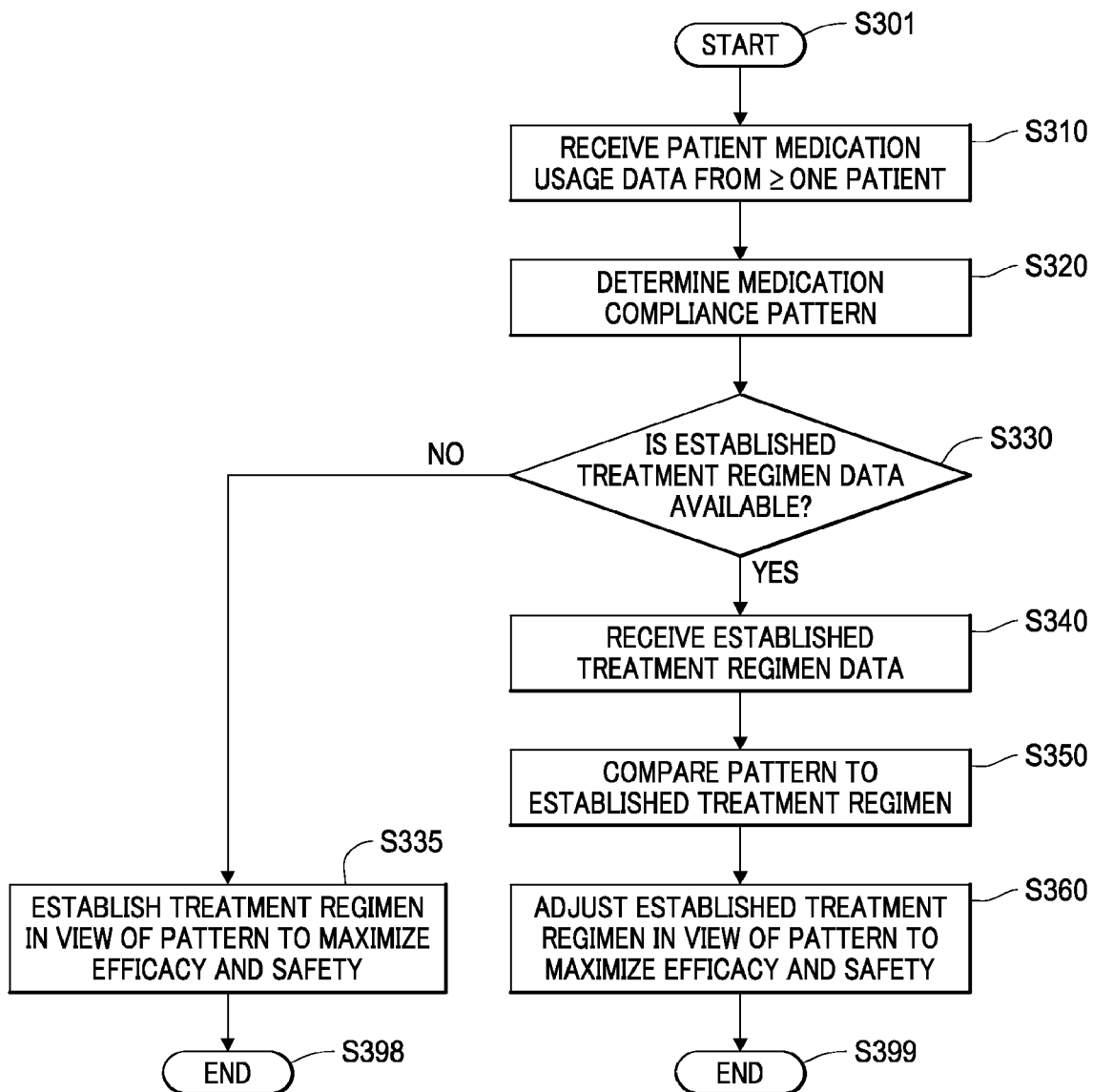
FIG. 3 is a flow diagram of a method of establishing a treatment regimen in accordance with an exemplary embodiment.

FIG. 3 shows a method of establishing a medication treatment regimen in accordance with an exemplary embodiment. The method may be carried out using a medication monitor and/or medication usage monitoring system as described herein. At S301, a system or apparatus may monitor the patient's or a population's usage of a medication to generate patient medication usage data. The patient medication usage data may be received at S310 at or from a medication monitor as described herein. The medication monitor may hold and monitor a single medication, or multiple medications. The patient medication usage data may relate to the single medication or to multiple medications. The patient medication usage data may relate to a single patient, or the patient medication compliance pattern data may relate to a population of patients. The usage data may concern the amount of dosage forms in a container at a given time, and may concern the time, date, and/or location at which a medication is removed from the container.

In exemplary embodiments, methods, systems, and apparatus may be directed to non-prescription or prescription applications including but not limited to immuno-suppressant, steroid, prednisone, microbicide, yeast infection, depression, schizophrenia, bipolar, anxiety, panic, mood stabilizer, schizophrenia, sleep apnea, epilepsy and other treatment regimens. Further, applications may include but are not limited to thyroid, contraceptive, diabetes Type I and Type II, heart failure, injectable medication, hypertension, acute myocardial infarction, anticoagulation, antibiotic, oncology, renal failure, tuberculosis, rheumatoid arthritis, post-surgery, geriatric, obesity, Alzheimer, HIV, lipid and cholesterol lowering, pain therapy, gastro-esophageal reflux disease, duodenal ulcer and H. Pilori, asthma, rhinitis and allergy, prostate, ADD, ADHD, ophthalmic, overactive bladder, gout, erectile dysfunction, vitamin, osteoporosis, smoking cessation, migraine, angina, and/or alcoholism treatment regimens.

The patient medication usage data may be organized for presentation in a format that accommodates determining a patient medication compliance pattern by way of, for example, graphical and/or diagrammatical representations of patient medication usage data. The patient medication usage data may be analyzed to determine a patient medication compliance pattern as shown at S320 of FIG. 3. The patient medication compliance pattern may be determined by way of a processor, using, for example, a computer-run algorithm.

At S330, a determination is made as to whether an established treatment regimen is available. The established treatment regimen may be a regimen previously prescribed for the monitored patient, or may be a recommended treatment regimen that has not previously been prescribed for the patient. If an established treatment regimen is available, the established treatment regimen is received at S340. The established treatment regimen may be received, for example, from a medication supplier, patient's caregiver, e.g., by way of a personal computer, a handheld device, or a centralized database. If established treatment regimen data is received at S340, then the established treatment regimen may be adjusted to maximize efficacy and safety, which may be determined by comparing the patient medication compliance pattern determined at S320 and the established treatment regimen received at S340.

Specifically, the patient medication compliance pattern determined at S320 and the established treatment regimen received at S340 may be compared at S350. Outcomes data and medication properties data may also be received, analyzed, and/or stored. The comparison may be carried out by way of a processor and computer-run software. Alternatively, patient medication compliance pattern data and outcomes data may be organized and formatted for presentation to a health care provider, caretaker or other interested party such as a family member. This may include ranking or assigning values to various aspects of the data to emphasize such aspects to caretakers or other interested parties.

Various algorithm techniques may be employed for analyzing the patient medication compliance pattern data and received established treatment regimen data. Exemplary techniques include traditional statistical methods, multiple linear regression models, simple mixed logistic regression analysis, generalized linear mixed effects models, marginal models and generalized estimating equations, models for longitudinal data analysis, support vector machines, neural networks, K-nearest neighbor interpolation, non-linear methods, and other methods as discussed above.

The algorithms may effect in part the step of establishing a new treatment regimen at S335, and/or the step of establishing a treatment regimen by adjusting an established treatment regimen at S360. Further the algorithms may provide a result at S398 or S399 of providing warnings, messages, and/or information to patients, family, caretakers, support organizations, medication developers or other interested parties. The algorithms may output status reports to interested parties, or result in a recommendation for the adjustment of a treatment regimen, e.g., in frequency and/or amount of dosage, and/or the type and/or number of medications prescribed. The status reports may include warnings, recommendations, or updated information. A remote communication device, receiving system, and/or medication container, for example, may receive warning messages. The status reports may be output from the algorithms. Further, the algorithms may output orders for specific tests or measures, or may output data upon which requests for such orders may be placed.

Figure 4:
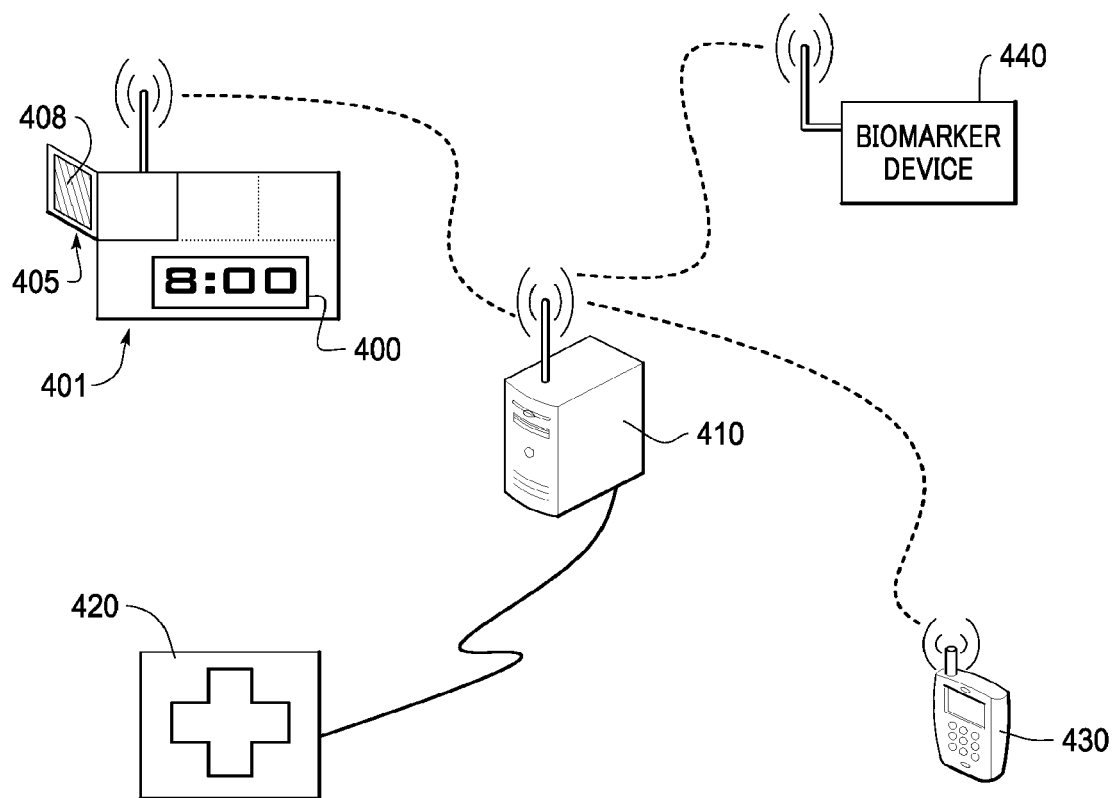
FIG. 4 is a diagrammatical view of a medication usage monitoring system in accordance with an exemplary embodiment.

FIG. 4 shows a treatment regimen compliance monitoring system having a medication monitor 401, and a receiving system 410. The receiving system 410 may be in communication with a storage system such as, for example, a server 420. The receiving system 410 may also be in communication with, for example, a reporting system 430. The receiving system 410 may also be in communication with a biomarker device 440. Any or all of the receiving system 410, the medication monitor 401, the server 420, the biomarker device 440, and the reporting system 430 may communicate by a wireless connection, wired connection, or a combination thereof, over the internet, local area network, PSTN, or the like.

The biomarker device 440 is preferably configured to output diagnostic test data related to a treatment regimen. Exemplary embodiments of the biomarker device 440 may include a microchip that is implanted into the patient, a weight scale, a blood pressure monitor, or a patch provided on the surface of the patient's skin. Alternatively, an embodiment of the biomarker device 440 may include a device that is configured to receive a biological sample and then be plugged into an analysis device, for example a component of a cell phone or some other device such as the reporting system 430. Each of the previously mentioned embodiments of the biomarker device 440 may communicate by a wireless connection (such as through an RFID tag), wired connection, or a combination thereof, over the internet, local area network, PSTN, or the like. U.S. Patent Application Publication No. 2005/0033133 A1 discloses an example of an implantable microchip that can detect and wirelessly transmit diagnostic test results. The disclosure of U.S. Patent Application Publication No. 2005/0033133 A1 is incorporated herein by reference in its entirety.

When the biomarker device 440 is implanted into the patient, the biomarker device 440 may be exposed to a source of bodily fluids such as blood in a vein, capillary, small artery or another fluid source such as urine or lymph fluid. The biomarker device 440 may detect, for example, blood glucose levels or an amount of medication in the blood and then may wirelessly transfer that information to the receiving system 410 and/or the reporting system 420.

The diagnostic test data output by the biomarker device 440 can then be used by a healthcare provider to understand a patient's individual medication compliance patterns and/or effects thereof, and thereby perform, establish and/or adjust of the patient's treatment regimen.

Medication monitor 401 may include a lid 405 having a transparent window 408. The transparent window 408 may enable viewing of a medication contained by the medication container 401. Further, medication monitor 401 may be constructed to house multiple medications separately or together, and may be configured to separately monitor each of the housed medications. Medication monitor 401 may be constructed to house one or more medications in various dosage forms. For example, medication monitor 401 may be constructed to house and dispense oral suspension, injection, inhalation, gel, cream, and/or solid dosage forms.

The medication monitor 401 may include a display 400. The display 400 may be, for example, a liquid crystal display that functions to present data generated or received by the medication monitor 401, or other information. Lid 405 may alternatively or additionally include a display 400. The lid 405 may be constructed to slideably and/or hingedly move between an open state and a closed state to accommodate access to and closure of one or more compartments of the medication monitor 401, thereby enabling a user to view the display while viewing and/or accessing at least one compartment of the medication monitor 401.

The medication container 401 may be battery powered, may include a SIM card, and/or may be GPS enabled. Medication container 401 may be a micro-electronic "smart" pill box that accepts a unique compartmentalized pill container insert that can either be hand-loaded with individual dosage forms of medications, or alternatively, the pill box can accept a custom designed, pre-filled cartridge. The pre-filled cartridge may include RFID labels that the medication container 401 can read to confirm the identity and/or amount of the medication contained in the pre-filled cartridge as an anti-counterfeiting measure to determine whether the pre-filled cartridge is authentic. Medication container 401 may be constructed to contain one or more types of medications that are each compartmentalized for ease of patient identification, dispensing, and refilling. The medication container 401 may for example, be constructed of aesthetically and ergonomically designed injection molded thermoplastic. The medication container itself and/or a cartridge/magazine for it may be childproof or tamperproof, and/or the monitor may be usable with childproof and/or tamperproof containers. The childproof/tamperproof features may be mechanical, electronic, electromechanical or other. For example, they may involve one or more biometric identification features, such as a fingerprint recognition lock, and/or electronic codes, and may optionally include time lock features to help control untimely or excess access to the contained medication.

Figure 5A:
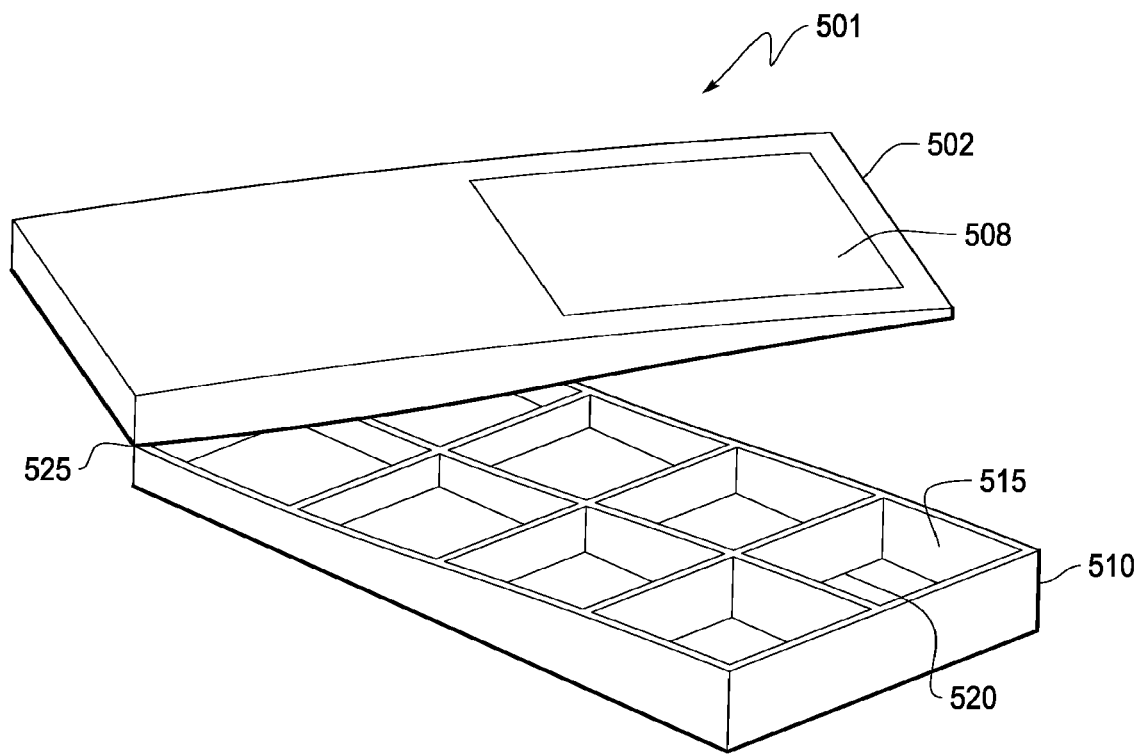
FIGS. 5a-5b are perspective views of a medication monitor in accordance with an exemplary embodiment.

FIG. 5A shows a preferred medication usage monitor 501 having a body 510. The body 510 may include a housing 515. The housing 515 may include one or more compartments 520. The medication usage monitor 501 may include a lid 502. The lid 502 may include a display 508. The display 508 may be, for example, a liquid crystal display, or any other suitable display now known or later developed. The lid 502 may be attached to the body 510 with a pivot 525 whereby the lid 502 may slideably move to cover or uncover the housing 515 of the body 510.

Figure 5B:
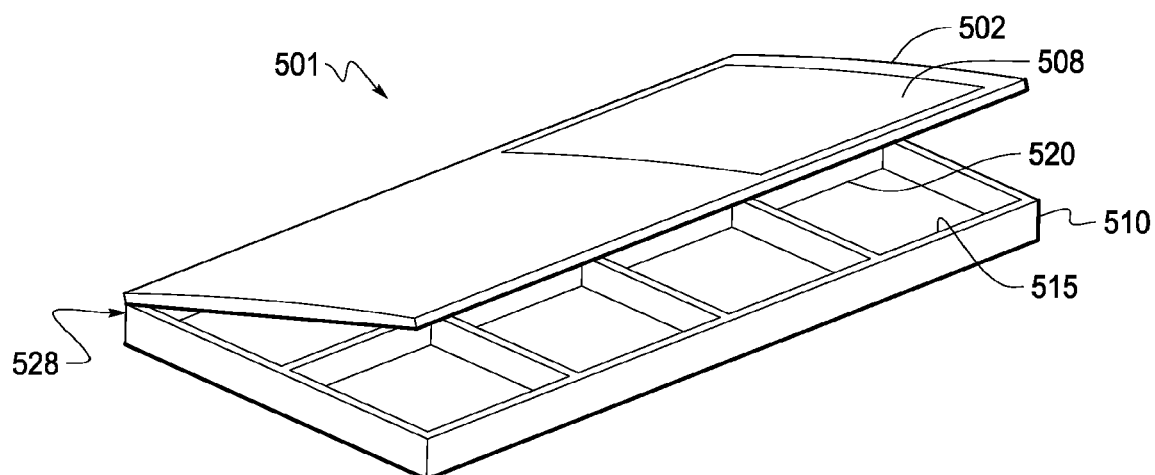

FIG. 5B shows medication monitor 501, which may include a lid 502. The lid 502 may include a display 508. The display may be, for example, a liquid crystal display, or any other suitable display now known or later developed. The lid 502 may be attached to the body 510 by a hinge 528 so that the lid 502 may be lifted upward with respect to the body 510 to provide access to the housing 515 and one or more compartments 520 located therein. The housing 515 may be constructed to receive and retain medication dosage forms, medication containers, medication cartridges that are factory refilled and/or refillable by consumers, and/or blister packs containing medication. One or more sensor may be provided to determine when medication is removed from the housing; such sensors may be specific to opening of or dosage removal from a single compartment, or from any of several compartments.

The medication monitor 501 may serve as a periodic dispensing device. The medication monitor 501 may also serve as a monitor for determining medication refill needs and communicating related messages. The medication monitor 501 may be one unit or multiple units, and may include multiple containers or compartments for organizing multiple medications. If multiple units are provided to a single patient, they preferably are capable of communicating, and programmed to communicate, with one another to ensure integrated reporting of usage data. The medication monitor 501 may be sized to fit in a pocket, or a purse, or may be larger. The medication monitor 501 may be constructed to hold and organize portable medication monitors. It may optionally include one or more processors as described above.

Figure 6:
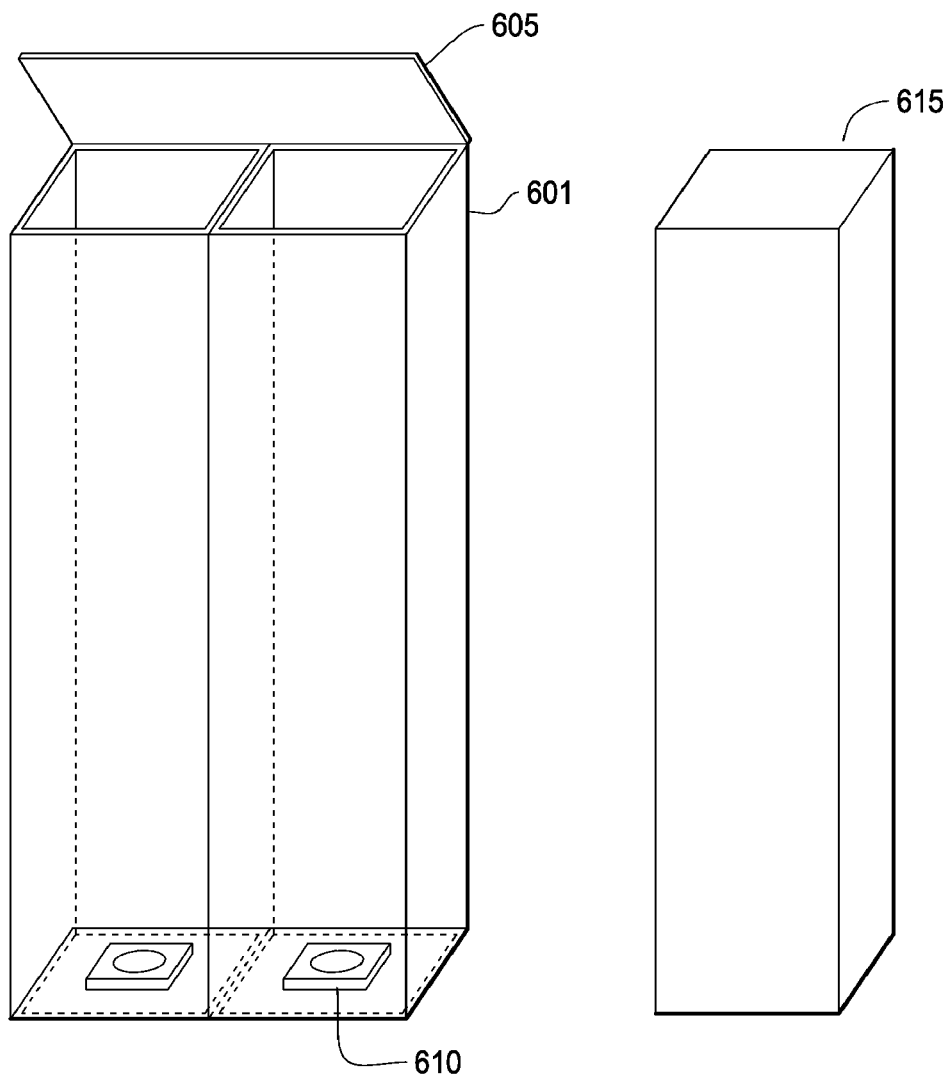
FIG. 6 is a perspective view of a medication monitor cartridge compartment in accordance with an exemplary embodiment.

FIG. 6 shows a medication cartridge. The medication cartridge may be constructed to be inserted into and/or removed from the medication monitor. The medication cartridge may be pre-filled with medication and/or refillable. The cartridge may accommodate any dosage form. In one version of the cartridge, 610 is a spring or other mechanism that keeps pushing the stacked pills up so that one or more pills can be removed at a time when the cartridge is opened. In another version of the cartridge, 610 is a mechanism with an opening that allow one or more pills to be removed from the medication monitor. In this version, the spring or other mechanism may be contained in the package or magazine of stacked of pills. Either mechanism may also contain a sensor (optic or other) that senses when a pill is removed from the magazine or cartridge. A pre-filled medication cartridge 615 according to embodiments is illustrated in FIG. 6. The pre-filled medication cartridge 615 may have a specific shape to match a specific shape of a housing of the medication monitor. The monitor may include a sensor to detect, for example, an origin of manufacture and/or identity of contents of the pre-filled medication insert 615. Each pre-filled medication insert 615 may have a barcode, an RFID tag, or other information source that relays the origin of manufacture data and/or other data, for example to verify authenticity and/or identity of the medication. The monitor may also include a sensor to detect a specific shape of a medication, the specific shape of the pre-filled medication insert 615, a medication made by a unique manufacturing process, or an orientation of the medication within the housing body as a way of protecting against counterfeiting and/or misuse of medication. The monitor may also include a barcode reader, an RFID label reader, or another information detector that allows for verifying whether the medication is counterfeit and/or the correct medication at the time of loading of the monitor and/or at the time of use by the patient. In addition to forwarding compliance data, the monitor may also send the information read by the reader to a receiving system such as a remote server, preferably the same remote server as discussed above, to verify whether the medication is authentic and/or the correct medication. The receiving system may compare the information received to the information in a database, and report issues to the patient and/or family, caretakers, support organizations, health care providers, etc.

The medication monitor may have one or more cartridges, which may or may not be separable as shown in FIG. 6. These multiple cartridges may hold the same drug (for example if higher doses or multiple pills are needed at a dose time) or different drugs. In one version there may be a mechanical mechanism in the medication monitor which slides past 610 of each cartridge, removing one or more pill (the pills can be different thicknesses and/or can be dispensed in groups) from each cartridge; the mechanism may be controlled mechanically or electromechanically. The magazine may be packaged with pills of existing shape and design, or pills may be designed with specific dimensions and characteristics allowing for pills to interface properly with packaging magazines, cartridges and/or medication monitors. The medication monitor may be configured to detect whether the pills provided in the magazine are authentic, for example, by detecting any one or a combination of size, shape, color, unique manufacturing process of the pills, or unique manufacturing process of the pre-filled cartridge, as a barrier to counterfeiting or improper filling (e.g., with an incorrect medication). The outer housing of the pre-packed magazine of pills may have vapor or other barrier properties necessary to maintain the stability of the medication contained in them.

The medication container 401 may include on-board micro-processing technology. The on-board micro-processing technology may function to record and/or report at least one of a time, a date, and a location of when a medication is inserted or removed, or a pre-loaded cartridge is inserted or removed, and/or other information as discussed herein. The micro-processing technology may function to record the number of medications or dosage forms in a specific medication compartment at any given time. The micro-processing technology may record a date, a location, and/or a time when the lid 408 is opened, and the date, the location, the time, and/or the amount when specific medication is removed or inserted. The micro-processing technology may function to determine medication compliance patterns, establish or recommend adjustment of treatment regimens in view of compliance data, medication properties data, and patient history data, and determine correlations between compliance data and patient history data, or those functions may be performed at a remote location.

Medication container 401 may include a transmitter 412 that effects communication of medication usage data or compliance patterns or other information discussed herein generated by the medication container 401. The transmitter may effect communication to at least one of the receiving device 410 and the server 420. The communication may comprise the information recorded by the micro-processing technology of the medication monitor 401, a biomarker device, and/or other information input by a patient or caregiver. Medication monitor 401 may include a port for communicating data, for example, wirelessly or by a Universal Serial Bus connection.

Information may be transmitted from the monitor 401 to a receiving system 410. The receiving system 410 may include a communications port such as a transceiver for receiving information and transmitting information to the reporting system 430 and/or the server 420. The receiving system 410 may include, for example, a port for communicating wirelessly or over a Universal Serial Bus connection. The receiving system 410 may include a remote storage system that receives and stores information from at least one of the medication monitor 401 and the receiving system 410. The receiving system 410 and/or remote storage device may implement algorithms to analyze information such as medication usage data, established treatment regimen data, medication properties data, and patient history data, including outcomes data. Outcomes data may be received by receiving system 410 from, for example, server 420 or a healthcare provider, whether private or publicly accessible. A monitored patient's attending physician, healthcare system representative, or laboratory information system, a data collection center, or the like may electronically provide a patient's outcomes data to the receiving system. Medication properties data such as medication interaction data may be received from a central database or other repository of medication interaction data.

The algorithms used in methods, apparatus and systems described herein may be designed to determine a medication compliance pattern, or to analyze a medication compliance pattern received from the medication monitor 401. Further, the algorithms may be designed to correlate one or more patient medication compliance patterns with outcomes data, which also may be analyzed by way of the algorithms. Still further, the algorithms may analyze medication interaction data in view of outcomes data and medication compliance patterns to accommodate treatment regimen establishment and/or adjustment. Algorithms may also organize outcomes data, medication usage data, treatment regimen compliance patterns, and/or a combination thereof for presentation to a caretaker or other interested party. The organization may be effected by a ranking system in which values are attributed to aspects of the data to signify a level of importance to a caretaker or other interested party. For example, an output of an algorithm executed in accordance with an exemplary embodiment may be a warning that may be sent to at least one of a medication monitor 401, receiving system 410, server 420, and reporting system 430. The presentation may be textual, graphical, auditory, and/or diagrammatic. The data may be presented, for example, on a laptop, desktop or workstation computer display, or may be presented on a handheld device such as reporting system 430.

For example, an exemplary algorithm for methods, systems, and apparatus may include inputting a starting dosing regimen of a medication for treatment of a particular condition. Then, compliance patterns may be input. Medication properties data and patient history data may also be input. The algorithm may output, based on compliance patterns, medication properties data, and/or patient history data a new regimen or report.

For example, for a kidney transplant recipient (patient) with a safety risk of malignancy or infection, the algorithm may include the step of inputting a starting dosing regimen of cyclosporin A at x mg per day to provide post kidney transplant immunosuppression. The compliance pattern may be input, which may indicate that the patient has a pattern of high compliance with very few missed doses. The medication properties data and patient history data, including patient physical data (e.g., weight, body mass index, gender, etc.), patient cyclosporin A measurements, and other data, may be input. The algorithm may also consider malignancy and infection risk data linked to population compliance patterns. Taking these variables into account, the algorithm may then output a new treatment regimen that includes lowering a dose amount of the medication to y mg per day. Alternatively, the treatment regimen may be changed to one that is not correlated with malignancy or infection in view of the duration of the given patient's high compliance pattern.

Over time, the database is populated with information from patients who have had malignancies or infections correlatable to variations among their individual compliance patterns. Specific compliance patterns that have a high probability of resulting in malignancies or infections are identified and are included in the algorithm. The algorithm routinely assesses each individual's ongoing compliance pattern. When an individual pattern is developing a correlation with a malignancies-or infections-related pattern, the algorithm outputs an appropriate and/or pre-established dose reduction and/or other treatment regimen change.

The algorithm may utilize models or subroutines in addition to assessing direct relationships between compliance patterns and malignancies or infections. For example, if individual drug levels (from therapeutic drug monitoring) are available, pharmacokinetic models (single compartment and others) can be utilized to project the resulting dynamic drug levels for the specific individual based on the specific individual's compliance pattern, allowing intervention to be engaged prior to a malignancy or infection event when projected drug exposure is too high. This approach can also be utilized with appropriate PK and/or ADME models when the patient is also prescribed other medications that may have drug-drug interactions such as inducing or inhibiting drug metabolism. As the database expands and includes existing and future biomarkers of malignancy or infections, the algorithm may establish relationships between individual compliance patterns and resulting changes in these biomarkers, allowing for the engagement of interventions (e.g., dose reduction) prior to a malignancy or infection event.

In another example, a compliance pattern may show that a patient occasionally misses doses but takes medication consistently. The patient history data may show chronic rejection risk associated with the compliance pattern, and also show chronic allograft nephropathy data indicating histological tubulointestinal fibrosis and tubular atrophy. The algorithm may output a new dosing regimen that increases the dose, and/or the treatment regimen may be changed to one that is not correlated with chronic rejection with the given patient's specific compliance pattern.

Over time, the database is populated with information from patients who have had chronic rejection correlatable to variations among their individual compliance patterns. Specific compliance patterns that have a high probability of resulting in chronic rejection are identified and are included in the algorithm. The algorithm routinely assesses each individual's ongoing compliance pattern. When an individual pattern is developing a correlation with a chronic rejection-related pattern, the algorithm outputs an appropriate and/or pre-established dose increase and/or other treatment regimen change.

The algorithm may utilize models or subroutines in addition to assessing direct relationships between compliance patterns and chronic rejection. For example, if individual drug levels (from therapeutic drug monitoring) are available, pharmacokinetic models (single compartment and others) can be utilized to project the resulting dynamic drug levels for the specific individual based on the specific individual's compliance pattern, allowing intervention to be engaged prior to the chronic rejection. The intervention may be a behavioral intervention to change the individual's compliance pattern and/or dose amount and/or other treatment regimen changes (e.g., prohibiting administration of certain types of medications). As the database expands and includes existing and future biomarkers of chronic rejection, the algorithm may establish relationships between individual compliance patterns and resulting changes in these biomarkers, allowing for the engagement of interventions (e.g., dose increase) prior to a rejection event.

In another example, a patient with a risk of acute rejection may be given a starting dosing regimen of a drug for post kidney transplant immunosuppression. A compliance pattern that is input may show that the patient has had many missed doses and periods of missed doses. Medication properties data and patient history data may be input. The medication properties data, patient history data, and compliance pattern may be analyzed to determine and output an intervention prior to acute rejection of the transplanted kidney. For example, the intervention may be warning messages to the patient, family, support organizations; change of medications; change of dosage timing and/or amounts; and the like.

Over time, the database is populated with information from patients who have undergone acute rejection correlatable to variations among their individual compliance patterns. Specific compliance patterns that have a high probability of resulting in acute rejection are identified and are included in the algorithm. The algorithm routinely assesses each individual's ongoing compliance pattern. When an individual pattern is developing a correlation with an acute rejection-related pattern, the algorithm outputs an appropriate and/or pre-established intervention.

The algorithm may utilize models or subroutines in addition to assessing direct relationships between compliance patterns and acute rejection. For example, if individual drug levels (from therapeutic drug monitoring) are available, pharmacokinetic models (single compartment and others) can be utilized to project the resulting dynamic drug levels for the specific individual based on the specific individual's compliance pattern, allowing intervention to be engaged prior to the acute rejection event, for example when the drug exposure is too low or too intermittent. As the database expands and includes existing and future biomarkers of acute rejection, the algorithm may establish relationships between individual compliance patterns and resulting changes in these biomarkers, allowing for the engagement of interventions prior to an acute rejection event.

The medication usage data, medication interaction data, outcomes data, and medication compliance pattern(s) analyzed by the algorithms of the receiving system 410 may be made available to a patient's physician or other interested party by way of a secure website. A healthcare provider may understand a patient's individual medication compliance patterns and thereby perform informed establishment and/or adjustment of the patient's treatment regimen. Over time, as data builds on compliance patterns for populations of patients in specific disease states, such pattern data forms a registry that can provide profound insights into the relationship between patient medication compliance patterns and treatment regimens with individual patient medical outcomes or population medical outcomes. For example, such a database of patients with common disease indications can be a profound resource for improving public health and lowering the cost of medicine in specific disease states.

Using immunosuppressants in transplant as an example, over the past 20 years improvements in the kidney transplant and post transplant care process have improved 1-year graft survival rates, yet long term graft survival rates (5 years or greater) have not improved. A significant cause of the long term graft failures is declining medication compliance by individual patients. By utilizing methods, systems, and/or apparatus described herein, many of these long term graft failures can be prevented, avoiding the high cost of returning to dialysis and re-transplant.

EXAMPLES

The following are exemplary lists of variables that could be input into algorithms useful in practicing methods and systems disclosed herein.
1. General Variables
   a. Individual patient data
      i. Individual adherence patterns
         1. Pre-therapy with placebo
         2. Pre-therapy with existing drugs
         3. While on therapy ii. Other
  1. Physical
   a. Weight
   b. Body mass index
   c. Gender
   d. Other
  2. Physiological
   a. ADME data for any of the drugs patient takes
   b. Other
b. Population or group adherence patterns
c. Network performance data
d. Drug specific for target disease
 i. Efficacy variables
 ii. Safety variables
e. Disease Physiological specific
 i. Efficacy variables
 ii. Safety variables
f. Drug specific for co-morbid diseases (individual drugs and drug-drug interactions)
 i. Efficacy variables
 ii. Safety variables
g. Disease Physiological specific for co-morbidities (individual drugs and drug-drug interactions)
 i. Efficacy variables
 ii. Safety variables
h. Patient support organization
i. Co-morbidity data
j. Patient social support network
k. Travel or time zone changes
 2. Exemplary variables for transplant immunosuppressant (TI) therapy
a. Individual patient data
 i. Individual adherence patterns
  1. Pre-therapy with placebo
  2. Pre--therapy with existing drugs
  3. While on therapy
 ii. Other
  1. Physical
   a. Weight
   b. Body mass index
   c. Gender
   d. Other
  2. Physiological
   a. ADME data for any of the drugs patient takes
   b. Other
    i. HLA matching data
    ii. Smoking status
b. Population or group adherence patterns
c. Network performance data
d. Drug specific for target disease
 i. Prescribed dose information (amount, frequency)
 ii. Efficacy variables
  1. Drug plasma levels
   a. Calcineurin Inhibitors (CNI)
    i. CSA (cyclosporine)
     1. e.g., initially, levels in the range of 10-20 ng/mL, but, after 3 months, levels are kept lower (5-10 ng/mL) to reduce the risk of nephrotoxicity.
    ii. Tacrolimus
    iii. Mycophenolate mofetil (MMF)
   b. Steroids
   c. OKT3 (Muromonab CD3) levels
   d. Sirolimus
   e. Everolimus
   f. Mercaptopurine
 iii. Safety variables
  1. Interstitial fibrosis due to CNI nephrotoxicity
  2. CSA
   a. Nephrotoxicity markers
    i. BUN
    ii. Creatinine
    iii. Urinary cystatin C
    iv. Urinary β2-microglobulin
    v. Urinary protein
    vi. Kidney Injury Marker (KIM 1)
    vii. Urinary N-acetyl-glucosamine
    viii. Glycosuria
   b. Cardiotoxicity markers
   c. Hyperlipidemia markers
   d. Markers for adverse effects including hyperkalemia, hypomagnesemia, nausea, vomiting, diarrhea, hypertrichosis, hirsutism, gingival hyperplasia, hyperlipidemia, glucose intolerance, infection, malignancy, and hyperuricemia
   e. Markers for adverse effects due to multiple drug interactions, primarily with agents affecting the cytochrome P-450 system.
  3. Tacrolimus
   a. Nephrotoxicity markers
   b. Cardiotoxicity markers
    i. QT prolongation
   c. Hyperlipidemia markers
   d. Markers for adverse effects including neurotoxicity, glucose intolerance
   e. Markers for adverse effects due to multiple drug interactions, primarily with agents affecting the cytochrome P-450 system
  4. Mycophenolate acid (MCA) and MMF
   a. Markers for adverse effects including nausea, vomiting, diarrhea, leucopenia, anemia, and thrombocytopenia
  5. Steroids
   a. Cushing disease, bone disease (eg, osteoporosis, avascular necrosis), cataracts, glucose intolerance, infections, hyperlipidemia, and growth retardation
  6. Azathioprine (derivative of 6-mercaptopurine)
   a. leucopenia, thrombocytopenia, GI difficulties, hepatitis, cholestasis, and alopecia
   b. Watch CBC counts carefully when withdrawing steroids
   c. Decrease the dose if azathioprine is administered with allopurinol
   d. Monitor CBC counts and pancreatic and liver enzyme levels
  7. Sirolimus
   a. Markers for adverse effects including hyperkalemia, hypomagnesemia, hyperlipidemia, hypertriglyceridemia, leucopenia, anemia, impaired wound healing, and joint pain
   b. Markers for adverse effects due to multiple drug interactions, especially because of the extremely long half-life.
  8. Muromonab-CD3 (OKT3)
   a. Markers for adverse effects due to cytokine release syndrome (ie, fever, dyspnea, wheezes, headache, hypotension), pulmonary edema, fever, chills, thrombocytopenia, leucopenia, hemolysis, respiratory distress, serum sickness, and anaphylaxis e. Disease Physiological specific
  i. Efficacy variables
    1. Acute rejection rate
      a. Early
      b. Late
      c. Number of episodes
    2. Vascular rejection
    3. CNI dosing data
    4. Chronic allograft nephropathy (CAN)
      a. Histological changes
      b. Interstitial fibrosis and tubular atrophy (IF/TA)
      c. Vascular occlusive changes
      d. Glomerulosclerosis
    5. Monocyte data (CD40,CD80,CD4, CD68,CD154, CD86, other markers)
  ii. Safety variables
    1. Patient infection data (28% of transplant patients have infection in first year) and related tests (see BKV for specific example)
      a. CMV infections in kidney transplant
      b. HCV recurrence in Liver transplant
      c. BKV (BK polymavirus) infection and nephropathy develops in 5% (1-10%) of kidney transplants and can lead to loss of graft in 50%
        i. BKV-specific T-cell activity
          1. IFN-γ, production using ELISpot
          2. intracellular cytokine staining and FACS analysis
        ii. BK viral load
          1. Urine tests
          2. Blood tests
    2. Patient Oncology data
      a. Non-melanoma skin cancers (NMSC)
      b. Lymphoma data
        i. Acute myeloid leukemia (AML)
        ii. Myelodysplastic syndromes (MDS)
      c. Malignancy post liver transplant
      d. Malignancy post kidney transplant
      e. Malignancy post heart transplant
      f. Malignancy post pancreas/Islet transplant
      g. Malignancy post lung transplant
      h. Malignancy post other transplant
f. Drug specific for co-morbid diseases (individual drugs and drug-drug interactions)
  i. Efficacy variables
    1. Hypertension drugs (50% of hypertensive transplant patients receive ACE inhibitors)
    2. High cholesterol drugs (60% of high cholesterol transplant patients receive statins)
    3. De novo or new onset diabetes (15% of transplant patients at year 1, increasing from 8%)
  ii. Safety variables
    1. Osteonecrosis (5-40% on steroids chronically get avascular osteonecrosis of the femoral head)
g. Disease physiological specific for co-morbidities (individual drugs and drug-drug interactions)
  i. Efficacy variables
    1. Blood pressure (and other) for hypertension
    2. Cholesterol and lipid levels (and other) for high cholesterol
    3. Weight (and other) for obesity
    4. Glucose, HbAl c and other tests for diabetes
  ii. Safety variables
h. Patient support organization
i. Co-morbidity data
  i. 33% of transplant patients have hypertension
j. Patient social support network
k. Travel or time zone changes The following are exemplary lists of applications (example medical specialties in parentheses) and patient types that could particularly benefit from implementation in methods and systems disclosed herein. In particular, pre-packaging of the identified medications with systems of the invention is contemplated.

1) Immunosuppressant (Transplantation Medicine, Rheumatology, Ophthalmology, Gastroenterology, Dermatology, Neurology)
  a. Medications
    i. Cyclosporine (Sandimmune®, Neoral, Gengraf, SangCya)
    ii. azathioprin (Imuran)
    iii. steroids or prednisone (Deltasone, Kedral, Medrol, Orasone, Prelone, Sterapred DS)
    iv. tacrolimus or FK506 (Prograf)
    v. mycophenolate mofetil (Cellcept)
    vi. sirolimus (Rapamune)
    vii. Methotrexate (Rheumatrex)
    viii. Leflunomide (Arava)
    ix. Cyclophosphamide (Cytoxan)
    x. Chlorambucil (Leukeran)
    xi. Nitrogen mustard (Mustargen)
  b. Patient groups
    i. Kidney Transplant Recipient
    ii. Heart Transplant Recipient
    iii. Liver Transplant Recipient
    iv. Pancreas/Islet cell Transplant Recipient
    v. Bone Morrow Transplant Recipient
    vi. Other Immunosuppressant indications (lupus, Myasthenia Gravis, Inflammatory Bowel Disease, Ulcerative Colitis, Psoriasis, Multiple Sclerosis)
  c. Indications
    i. Efficacy (system and algorithm address when compliance pattern is not adequate to maintain intended efficacy)
      1. Graft rejection
      2. Outcome measures; renal function biomarkers, graft rejection markers, blood level of medication (cyclosporine, tacrolimus)
    ii. Safety (system and algorithm address when compliance pattern is problematic)
      1. Infections (Pneumocystis pneumonia (PCP), BK virus), cancer and other consequences of over immunosuppression (Beyond immunosuppression, cyclosporine A promotes carcinogenesis by TGF beta and VEGF, while mTOR inhibitors are antiproliferative. Azathioprine photosensitizes to UVA and enables UVA to damage DNA directly.)
      2. Outcome measures: Incidence of infection/cancer/other events and biomarkers used to diagnose condition
2) Steroid or Corticosteroid or Prednisone (Transplantation, Dermatology, Hematology, Neurology, Hematology, Gastroenterology, Allergy and Immunology, Endocrine and Metabolism, Family Practice, General Practice, Geriatric, Rheumatology, Ophthalmology)
  a. Medications
    i. Deltasone® (prednisone) (Kedral, Medrol, Orasone, Prelone, Sterapred DS)
  b. Patient groups
    i. Nervous System-Acute exacerbations of multiple sclerosis Endocrine Disorders Primary or secondary adrenocortical insufficiency (hydrocortisone or cortisone is the first choice; synthetic analogs may be used in conjunction with mineral corticoids
ii. Congenital adrenal hyperplasia
Hypercalcernia associated with cancer
Nonsuppurative thyroiditis
iii. Rheumatic Disorders
As adjunctive therapy for short-term administration (to tide the patient over an acute episode or exacerbation) in: Psoriatic arthritis
Rheumatoid arthritis, including juvenile rheumatoid arthritis (selected cases may require low-dose maintenance therapy)
Ankylosing spondylitis
Acute and subacute bursitis
Acute nonspecific tenosynovitis
Acute gouty arthritis
Post-traumatic osteoarthritis
Synovitis of osteoarthritis
Epicondylitis
iv. Collagen Diseases
During an exacerbation or as maintenance therapy in selected cases of:
Systemic lupus erythematosus
Systemic-dermatomyositis (polymyositis)
Acute rheumatic carditis
v. Dermatologic Diseases
Pemphigus
Bullous dermatitis herpetiformis
Severe erythema multiforme
(Stevens-Johnson syndrome)
Exfoliative dermatitis
Mycosis fungoides
Severe psoriasis
Severe seborrheic dermatitis
vi. Allergic States
Control of severe or incapacitating allergic conditions intractable to adequate trials of conventional treatment:
Seasonal or perennial allergic rhinitis
Bronchial asthma
Contact dermatitis
Atopic dermatitis
Serum sickness
Drug hypersensitivity reactions
vii. Ophthalmic Diseases
Severe acute and chronic allergic and inflammatory processes involving the eye and its adnexa such as:
Allergic cornea marginal ulcers
Herpes zoster ophthalmicus
Anterior segment inflammation
Diffuse posterior uveitis and choroiditis
Sympathetic ophthalmia
Allergic conjunctivitis
Keratitis
Chorioretinitis
Optic neuritis
Iritis and iridocyclitis
viii. Respiratory Diseases
Symptomatic sarcoidosis
Loeffler's syndrome not manageable by other means
Berylliosis
Fulminating or disseminated pulmonary tuberculosis when used concurrently with appropriate antituberculous chemotherapy
Aspiration pneumonitis
ix. Hematologic Disorders
Idiopathic thrombocytopenic purpura in adults
Secondary thrombocytopenia in adults
Acquired (autoimmune) hemolytic anemia
Erythroblastopenia (RBC anemia)
Congenital (erythroid) hypoplastic anemia
x. Neoplastic Diseases For palliative management of:
Leukemias and lymphomas in adults
Acute leukemia of childhood
xi. Edematous States
To induce a diuresis or remission of proteinuria in the nephrotic syndrome, without uremia, of the idiopathic type or that due to lupus erythematosus
xii. Gastrointestinal Diseases
To tide the patient over a critical period of the disease in:
Ulcerative colitis
Regional enteritis
xiii Nervous System
Acute exacerbations of multiple sclerosis
c. Indications
i. Efficacy (system and algorithm address when compliance pattern is not adequate to maintain intended efficacy)
ii. Safety (system and algorithm address when compliance pattern is problematic)
1. Drug-induced secondary adrenocortical insufficiency may be minimized by gradual reduction of dosage
3) Microbicide (Obstetrics and Gynecology, Preventative Medicine, Contraception, Infectious Disease)
a. Medications
i. Microbicide gels
ii. St. Michaels Medical gel
b. Patient groups
i. STI (sexually transmitted infections) prevention
1. HIV
2. Gonorrhea
3. Chlamydia
4. Syphilis
5. Other
ii. Contraception
iii. Common vaginal infections
1. Candida albicans (yeast)
2. Bacterial vaginitis
3. Other
c. Indications
i. Efficacy (system and algorithm address when compliance pattern is not adequate to maintain intended efficacy)
ii. Safety (system and algorithm address when compliance pattern is problematic)
4) Yeast Infection (Obstetrics and Gynecology, Otorhinolaryngology, Infectious Disease)
a. Medications
i. Fluconazole (D1FLUCAN®)
ii. Miconazole (Monistat-Derm, Monistat Vaginal)
iii. Tioconazole (Vagistat Vaginal)
iv. Butoconazole (Femstat)
v. Clotrimazole (Femizole-7, Gyne-Lotrimin)

b. Patient groups
  i. Vaginal candidiasis (vaginal yeast infections due to Candida).
  ii. Oropharyngeal and esophageal candidiasis
  iii. Cryptococcal meningitis
c. Indications
  i. Efficacy (system and algorithm address when compliance pattern is not adequate to maintain intended efficacy)
  ii. Safety (system and algorithm address when compliance pattern is problematic)
    1. Hepatic injury: DIFLUCAN has been associated with rare cases of serious hepatic toxicity, including fatalities 5) Anti-depressant (Psychiatry, Obstetrics and Gynaecology, Family Practice, General Practice, Geriatric)
  a. Medications
    i. Selective serotonin reuptake inhibitors (SSRIs)
      1. fluoxetine hydrochloride (PROZAC®), paroxetine (Paxil), sertraline (Zoloft), citalopram (Celexa), fluvoxamine (Luvox), and escitalopram (Lexapro).
    ii. Dual-action antidepressants
      1. Venlafaxine (Effexor), duloxetine (Cymbalta)', Mirtazapine (Remeron)
    iii. Atypical antidepressants
      1. nefazodone (Serzone), trazodone (Desyrel), and bupropion (Wellbutrin).
    iv. Bipolar and psychotic depression
      1. ziprasidone (Geodon), risperidone (Risperdal), quetiapine (Seroquel), aripiprazole (Abilify), and paliperdone (Invega), Lithium (Eskalith, Lithobid), valproate (Depakene, Depakote), carbamazepine (Epitol, Tegretol), neurontin (Gabapentin), and lamictal (Lamotrigine)
    v. Monoamine oxidase inhibitors (MAOIs)
      1. phenelzine (Nardil) and tranylcypromine (Panlate)
    vi. Tricyclic antidepressants (TCAs)
      1. amitriptyline (Elavil), protriptyline (Vivactil), desipramine (Norpramin), nortriptyline (Aventyl, Pamelor), imipramine (Tofranil), trimipramine (Surmontil), and perphenazine (Triavil).
  b. Patient groups
    i. Major Depressive Disorder
    ii. Generalized Anxiety Disorder
  c. Indications
    i. Efficacy (system and algorithm address when compliance pattern is not adequate to maintain intended efficacy)
      1. Improvement in following symptoms: depressed mood, loss of interest in usual activities, significant change in weight and/or appetite, insomnia or hypersomnia, psychomotor agitation or retardation, increased fatigue, feelings of guilt or worthlessness, slowed thinking or impaired concentration, a suicide attempt or suicidal ideation.
    ii. Safety (system and algorithm address when compliance pattern is problematic)
      1. Clinical Worsening and Suicide Risk 6) Schizophrenia and Bipolar (Psychiatry, Obstetrics and Gynaecology, Family Practice, General Practice, Geriatric)
  a. Medications
    i. SEROQUEL® (quetiapine fumarate)
    ii. RISPERDAL® (risperidone)
    iii. ABILIFY® (aripiprazole)
    iv. LAMICTAL (lamotrigine)
    v. BUDEPRION XLT™ (bupropion hydrochloride)
    vi. ZYPREXA (olanzapine)
    vii. Depakote ER (divalproex sodium)
    viii. Clozapine
  b. Patient groups
    i. Schizophrenia
    ii. Bipolar disorder
  c. Indications
    i. Efficacy (system and algorithm address when compliance pattern is not adequate to maintain intended efficacy)
      1. RISPERDAL® can be administered once or twice daily. Initial dosing is generally 2 mg/day. Dose increases should then occur at intervals not less than 24 hours, in increments of 1-2 mg/day, as tolerated, to a recommended dose of 4-8 mg/day.
    ii. Safety (system and algorithm address when compliance pattern is problematic)
      1. A potentially fatal symptom complex sometimes referred to as Neuroleptic Malignant Syndrome (NMS)
        a. A potentially fatal symptom complex sometimes referred to as Neuroleptic Malignant Syndrome (NMS) has been reported in association with antipsychotic drugs. Clinical manifestations of MS are hyperpyrexia, muscle rigidity, altered mental status, and evidence of autonomic instability (irregular pulse or blood pressure, tachycardia, diaphoresis, and cardiac dysrhythmia).
      2. Leukopenia, Neutropenia and Agranulocytosis
      3. Hypothyroidism
      4. Others
        a. Hepatic failure resulting in fatalities has occurred in patients receiving valproic acid.
        b. Cases of life-threatening pancreatitis have been reported in both children and adults receiving valproate 7) Anxiety, panic, mood stabilizer, sleep, epilepsy (Psychiatry, Sleep Medicine, Obstetrics and Gynaecology, Neurology, Family Practice, General Practice, Geriatric)
  a. Medications
    i. XANAX® (CIV alprazolarn)
    ii. PROZAC® (fluoxetine hydrochloride)
    iii. Ambien® (zolpidem tartrate)
    iv. KLONOPIN® (clonazepam)
    v. Neurontin® (gabapentin)
    vi. Ativan® (lorazepam)
    vii. Diazepam(diazepam) Injection
    viii. LAMICTAL (lamotrigine)
    ix. AMRIX® (cyclobenzaprine hydrochloride) AMRIX is indicated as an adjunct to rest and physical therapy for relief of muscle spasm associated with acute, painful musculoskeletal conditions.
    x. LUNESTA® (eszopiclone)
    xi. Depakote ER (divalproex sodium)
  b. Patient groups
    i. Anxiety Disorders and Transient Symptoms of Anxiety
    ii. Panic disorder
    iii. Seizure and epilepsy Disorders
    iv. Post therapeutic Neuralgia c. Indications
  i. Efficacy (system and algorithm address when compliance pattern is not adequate to maintain intended efficacy)
  ii. Safety (system and algorithm address when compliance pattern is problematic)
    1. Because of the danger of withdrawal, abrupt discontinuation of treatment should be avoided
    2. Dependence and Withdrawal Reactions, Including Seizures
    3. Interference With Cognitive and Motor Performance
    4. Suicidal Behavior and Ideation
    5. Antiepileptic drugs (AEDs), including Neurontin, increase the risk of suicidal thoughts or behavior in patients
8) Thyroid (Endocrine and Metabolism, Obstetrics and Gynecology, Family Practice, General Practice, Geriatric)
  a. Medications
    i. Levothyroxine sodium
    ii. Synthroid
  b. Patient groups
    i. Thyroid Hormone replacement
      1. Hypothyroidism
      2. Pituitary TSH Suppression
  c. Indications
    i. Efficacy (system and algorithm address when compliance pattern is not adequate to maintain intended efficacy)
      1. The levothyroxine sodium dose is generally adjusted in 12.5-25 mcg increments until the patient with primary hypothyroidism is clinically euthyroid and the serum TSH has normalized
    ii. Safety (system and algorithm address when compliance pattern is problematic)
      1. Adverse reactions associated with levothyroxine therapy are primarily those of hyperthyroidism due to therapeutic overdosage
9) (Oral) Contraceptive (Obstetrics and Gynecology, Family Practice, General Practice)
  a. Medications
    i. YAZ® (drospirenone and ethinyl estradiol)
    ii. ORTHO TRI-CYCLEN® Lo Tablets (norgestimate/ethinyl estradiol)
    iii. TriNessa™ (norgestimate and ethinyl estradiol tablets)
    iv. Yasmin® 28 Tablets (drospirenone and ethinyl estradiol)
    v. NUVARING® (etonogestrel/ethinyl estradiol) Vaginal Ring
  b. Patient groups
    i. prevention of pregnancy in women who elect to use an oral contraceptive
    ii. treatment of moderate acne vulgaris in women at least 14 years of age c.
  c. Indications
    i. Efficacy (system and algorithm address when compliance pattern is not adequate to maintain intended efficacy)
      1. timing of daily dose is critical for efficacy
    ii. Safety (system and algorithm address when compliance pattern is problematic)
      1. Thrombophlebitis
      2. Arterial thromboembolism
      3. Pulmonary embolism
      4. Myocardial infarction
      5. Cerebral hemorrhage
      6. Cerebral thrombosis
      7. Hypertension
      8. Gallbladder disease
      9. Hepatic adenomas or benign liver tumors
10) Diabetes Type 2 (Endocrine and Metabolism, General Practice, Family Practice, Internal Medicine)
  a. Medications
    i. GLUCOPHAGE® (metformin hydrochloride)
    ii. ACTOS® (pioglitazone hydrochloride)
    iii. LANTUS® (insulin glargine [rDNA origin] injection)
    iv. Micronase® (glyburide)
    v. JANUVIA™ (sitagliptin)
  b. Patient groups
    i. adults and children with type 2 diabetes mellitus.
  c. Indications
    i. Efficacy (system and algorithm address when compliance pattern is not adequate to maintain intended efficacy)
      1. Micronase Titration to Maintenance Dose
        a. The usual maintenance dose is in the range of 1.25 to 20 mg daily, which may be given as a single dose or in divided doses. Dosage increases should be made in increments of no more than 2.5 mg at weekly intervals based upon the patient's blood glucose response.
    ii. Safety (system and algorithm address when compliance pattern is problematic)
      1. abnormal stools, hypoglycemia, myalgia, lightheaded, dyspnea, nail disorder, rash, sweating increased, taste disorder, chest discomfort, chills, flu syndrome, flushing, palpitation
      2. Thiazolidinediones, including ACTOS, cause or exacerbate congestive heart failure in some patients
11) Heart Failure (Cardiovascular, Geriatric, General Practice, Family Practice)
  a. Medications
    i. Diuretics
      1. DYAZIDE® (hydrochlorothiazide/triamterene)
      2. MICROZIDE (hydrochlorothiazide)
      3. LASIX® (furosemide)
      4. TOPROL-XL (metoprolol succinate)
    ii. ACE inhibitor
      1. PRINIVIL (Lisinopril), a synthetic peptide derivative, is an oral long-acting angiotensin converting enzyme inhibitor
      2. VASOTEC® (enalapril maleate)
    iii. Beta Blocker
      1. Lopressor® (metoprolol tartrate)
    iv. Angiotensin II receptor blocker
      1. Diovan (valsartan)
    v. Other
      1. LANOXIN® (digoxin) Injection
  b. Patient groups
    i. edema associated with congestive heart failure
  c. Indications
    i. Efficacy (system and algorithm address when compliance pattern is not adequate to maintain intended efficacy)
    ii. Safety (system and algorithm address when compliance pattern is problematic)
      1. Hyperkalemia 12) Injectable Meds (Rheumatology, Allergy and Immunology, Oncology, Endocrine and Metabolism, Internal Medicine, Sports Medicine)
   a. Medications
      i. Insulin
      ii. Humura and similar
      iii. Promethazine Hydrochloride Injection
      iv. Other (somatropin, adalimumab, sumatriptan, mecasermin, interferon, alfacon-1, tinzaparin, interferon alfa-2B, anakinra, enoxaparin, lutropin, menotropins, calcitonin, chorionic gonadotropin, peginterferon alfa-2a, alprostadil, interferon beta-1a, methylnaltrexone bromide, golimumab, pegvisomant, histrelin, liraglutide, leuprolide)
   b. Patient groups
   c. Indications
      i. Efficacy (system and algorithm address when compliance pattern is not adequate to maintain intended efficacy)
      ii. Safety (system and algorithm address when compliance pattern is problematic)
13) Hypertension ((Cardiovascular, Geriatric, General Practice, Family Practice, Internal Medicine)
   a. Medications
      i. Diuretics
         1. DYAZIDE® (hydrochlorothiazide/triamterene)
         2. MICROZIDE (hydrochlorothiazide)
         3. LASIX® (furosemide)
      ii. ACE inhibitor
         1. PRINIV1L (Lisinopril), a synthetic peptide derivative, is an oral long-acting angiotensin converting enzyme inhibitor
         2. ALTACE (ramipril)
         3. VASOTEC® (enalapril maleate)
      iii. Beta Blocker
         1. Lopressor® (metoprolol tartrate)
         2. TENORMIN (atenolol)
         3. TOPROL-XL (metoprolol succinate)
      iv. Combinations of meds
         1. Apresazide (Hydralazine HCl and hydrochlorothiazide)
         2. ZESTORETIC® (lisinopril and hydrochlorothiazide)
      v. Calcium channel blocker
         1. NORVASC® (amlodipine besylate)
         2. CARTIA XT™ (diltiazern hydrochloride)
         3. COVERA-HS® (verapamil hydrochloride)
      vi. angiotensin II receptor blocker
         1. Diovan (valsartan)
         2. AVAPRO® (irbesartan)
      vii. Other
         1. Benicar (olmesartan medoxomil)
         2. Catapres® (clonidine hydrochloride)
         3. Hyzaar (losartan potassium-hydrochlorothiazide)
         4. BENTCAR HCT® (olmesartan medoxornilhydrochlorothiazide)
         5. KLOR-CON® (potassium chloride) for the therapeutic use of patients with hypokalemia
         6. ZESTORETIC® (lisinopril and hydrochlorothiazide)
   b. Patient groups
      i. Hypertension
      ii. Angina Pectoris
      iii. Myocardial Infarction
   c. Indications
      i. Efficacy (system and algorithm address when compliance pattern is not adequate to maintain intended efficacy)
         1. Benicar Dosage must be individualized. The usual recommended starting dose of Benicar is 20 mg once daily when used as monotherapy in patients who are not volume-contracted. For patients requiring further reduction in blood pressure after 2 weeks of therapy, the dose of Benicar may be increased to 40 mg. Doses above 40 mg do not appear to have greater effect. Twice-daily dosing offers no advantage over the same total dose given once daily.
      ii. Safety (system and algorithm address when compliance pattern is problematic)
         1. NORVASC® (amlodipine besylate)
            a. Increased Angina or Myocardial Infarction
            b. Beta-Blocker Withdrawal
            c. Patients with Hepatic Failure
         2. Furosemide
            a. Gastrointestinal System Reactions: hepatic encephalopathy in patients with hepatocellular insufficiency, pancreatitis, jaundice (intrahepatic cholestatic jaundice), anorexia
         3. Dyazide (hydrochlorothiazide/triamterene)
            a. Abnormal elevation of serum potassium levels (greater than or equal to 5.5 mEq/liter) can occur with all potassium-sparing diuretic combinations, including Dyazide
         4. Clonidine Withdrawal
            a. Sudden cessation of clonidine treatment has, in some cases, resulted in symptoms such as nervousness, agitation, headache, and tremor accompanied or followed by a rapid rise in blood pressure and elevated catecholamine concentrations in the plasma
14) Acute Myocardial infarction (Cardiovascular, Geriatric, General Practice, Family Practice)
   a. Medications
      i. PRINIVIL® (lisinopril) a synthetic peptide derivative, is an oral long-acting angiotensin converting enzyme inhibitor
      ii. TENORMIN (atenolol)
      iii. Aspirin
      iv. NORVASC® (amlodipine besylate)
      v. TOPROL-XL (metoprolol succinate)
      vi. ALTACE (ramipril)
   b. Patient groups
      i. PRINIVIL is indicated for the treatment of hemodynamically stable patients within 24 hours of acute myocardial infarction
      ii. Coronary Artery Disease
      iii. Chronic Stable Angina
      iv. Vasospastic Angina (Prinzmetal's or Variant Angina)
   c. Indications
      i. Efficacy (system and algorithm address when compliance pattern is not adequate to maintain intended efficacy)
      ii. Safety (system and algorithm address when compliance pattern is problematic)
         1. PRINIVIL, consideration should be given to the fact that another angiotensin converting enzyme inhibitor, captopril, has caused agranulocytosis, particularly in patients with renal impaituient or collagen vascular disease 15) Anitcoagulation (Cardiovascular, Geriatric, General Practice, Hematology, Family Practice, Surgery)
   a. Medications
      i. Aspirin (acetylsalicylic acid)
      ii. Plavix (clopidogrel bisulfate)
      iii. COUMADIN® TABLETS (warfarin sodium)
   b. Patient groups
      i. Recent MI, Recent Stroke, or Established Peripheral Arterial Disease
      ii. Acute Coronary Syndrome
      iii. treatment of venous thrombosis and its extension, and pulmonary embolism
      iv. thromboembolic complications associated with atrial fibrillation and/or cardiac valve replacement
      v. thromboembolic events such as stroke or systemic embolization after myocardial infarction.
   c. Indications
      i. Efficacy (system and algorithm address when compliance pattern is not adequate to maintain intended efficacy)
         1. Treatment of each patient is a highly individualized matter. COUMADIN (Warfarin Sodium), a narrow therapeutic range (index) drug, may be affected by factors such as other drugs and dietary vitamin K. Dosage should be controlled by periodic determinations of prothrombin time (PT)/International Normalized Ratio (1NR). Determinations of whole blood clotting and bleeding times are not effective measures for control of therapy. Heparin prolongs the one-stage PT.
      ii. Safety (system and algorithm address when compliance pattern is problematic)
         1. Hemorrhagic or bleeding complications
         2. Thrombotic thrombocytopenic purpura (TTP)
16) Antibiotics (Infectious Diseases, Geriatric, General Practice, Family Practice, Surgery, Transplantation Medicine, Pulmonary)
   a. Medications
      i. Amoxicillin
      ii. Augmentin® (amoxicillin/clavulanate potassium)
      iii. ZITHROMAX® (azithromycin)
      iv. KEFLEX® (cephalexin)
      v. LEVAQUIN® (levofloxacin)
      vi. Septra Tablets (trimethoprim and sulfamethoxazole)
      vii. CIPRO® (ciprofloxacin hydrochloride)
      viii. PENICILLIN V POTASSIUM (penicillin v potassium)
      ix. CIPRO® (ciprofloxacin hydrochloride)
      x. DORYX® (doxycycline hyclate)
      xi. AVELOX® (moxifloxacin hydrochloride)
   b. Patient groups
      i. Acute short course treatment of patients with mild to moderate infections
      ii. Acute bacterial exacerbations of chronic obstructive pulmonary disease
      iii. Acute bacterial sinusitis
      iv. Community-acquired pneumonia
      v. Nosocomial Pneumonia
      vi. Acute Bacterial Exacerbation of Chronic Bronchitis
      vii. Skin and Skin Structure Infections
      viii. Chronic Bacterial Prostatitis
      ix. Complicated Urinary Tract Infections
      x. Other
   c. Indications
      i. Efficacy (system and algorithm address when compliance pattern is not adequate to maintain intended efficacy)
      ii. Safety (system and algorithm address when compliance pattern is problematic)
         1. Avoid the development of bacterial resistance
         2. Fluoroquinolones, including LEVAQUIN®, are associated with an increased risk of tendonitis and tendon rupture
         3. severe hepatotoxicity (including acute hepatitis and fatal events) have been received for patients treated with LEVAQUIN®
         4. Convulsions and toxic psychoses have been reported in patients receiving fluoroquinolones
17) Oncology (Oncology, Surgery, Geriatrics)
   a. Medications
      i. Oral chemotherapy meds
         1. GLEEVEC (imatinib mesylate)
         2. Tasigna® (nilotinib)
         3. Other (CAPECITABINE, CYCLOPHOSPHAMIDE, ETOPOSIDE, IDARUBICIN, VINORELBINE)
   b. Patient groups
      i. Gastrointestinal stromal tumor: GIST. A type of tumor that usually begins in cells in the wall of the gastrointestinal tract. It can be benign or malignant. Malignant GISTs can occur from the esophagus to the rectum, but occur most commonly in the stomach and small intestine.
      ii. Newly Diagnosed Philadelphia Positive Chronic Myeloid Leukemia (Ph+CML)
      iii. Ph+CML in Blast Crisis (BC), Accelerated Phase (AP) or Chronic Phase (CP) After Interferon-alpha (IFN) Therapy
      iv. Pediatric Patients with Ph+CML in Chronic Phase
      v. Ph+Acute Lymphoblastic Leukemia (ALL)
      vi. Myelodysplastic/Myeloproliferative Diseases (MDS/MPD
      vii. Aggressive Systemic Mastocytosis (ASM)
      viii. Hypereosinophilic Syndrome (HES) and/or Chronic Eosinophilic Leukemia (CEL)
      ix. Dermatofibrosarcoma Protuberans (DFSP)
      x. Kit+Gastrointestinal Stromal Tumors (GIST)
      xi. Adjuvant Treatment of GIST
   c. Indications
      i. Efficacy (system and algorithm address when compliance pattern is not adequate to maintain intended efficacy)
      ii. Safety (system and algorithm address when compliance pattern is problematic)
         1. GLEEVEC (imatinib mesylate)
            a. Fluid Retention and Edema
            b. Hematologic Toxicity
            c. Severe Congestive Heart Failure and Left Ventricular Dysfunction
            d. Hepatotoxicity
            e. Hemorrhage
            f. Gastrointestinal Disorders
            g. Hypereosinophilic Cardiac Toxicity
            h. Dermatologic Toxicities
            i. Hypothyroidism
         2. Tasigna® (nilotinib)
            a. Myelosuppression
            b. QT Prolongation
            c. Sudden Deaths
            d. Elevated Serum Lipase
            e. Hepatotoxicity f. Electrolyte Abnormalities
g. Drug Interactions
h. Food Effects
  i. The bioavailability of nilotinib is increased with food. Tasigna should not be taken with food. No food should be taken at least 2 hours before and at least one hour after the dose is taken. Grapefruit products and other foods that are known to inhibit CYP3A4 should be avoided.
i. Hepatic Impairment
j. Lactose 18) Renal Failure (Nephrology, Internal Medicine, Cardiovascular, Geriatric)
  a. Medications
    i. Oral meds taken with dialysis (erythropoietin hormone, vitamin D, phosphate binders, vitamin C, B-complex vitamins and folic acid)
  b. Patient groups (people with chronic kidney disease (CKD), and patients with end stage renal disease (ESRD))
  c. Indications
    i. Efficacy (system and algorithm address when compliance pattern is not adequate to maintain intended efficacy)
    ii. Safety (system and algorithm address when compliance pattern is problematic)

19) Tuberculosis (Pulmonary, Infectious Disease)
  a. Medications
    i. Individual meds
    ii. Combination regimens (standard "short" course treatment for TB is isoniazid, rifampicin, pyrazinamide, and ethambutol for two months, then isoniazid and rifampicin alone for a further four months), (If the organism is known to be fully sensitive, then treatment is with isoniazid, rifampicin, and pyrazinamide for two months, followed by isoniazid and rifampicin for four months. Ethambutol need not be used).
  b. Patient groups (The risk factors for acquiring TB include close-contact situations, alcohol and IV drug abuse, and certain diseases (for example, diabetes, cancer, and HIV) and occupations (for example, health-care workers)).
  c. Indications
    i. Efficacy (system and algorithm address when compliance pattern is not adequate to maintain intended efficacy)
    ii. Safety (system and algorithm address when compliance pattern is problematic) The single biggest problem with TB treatment is drug-induced hepatitis, which has a mortality rate of around 5%.

20) Rheumatoid arthritis (Rheumatology, Geriatric, Family Practice)
  a. Medications
    i. Celebrex® (celecoxib)
    ii. MOTRIN® (ibuprofen)
    iii. Mobic® (meloxicam)
    iv. Methotrexate
      1. Brand Name: Trexall
         Generic Name: Methotrexate
      2. Brand Name: Rheumatrex
         Generic Name: Methotrexate Tablets
      3. Brand Name: Arava
         Generic Name: Leflunomide
      4. Brand Name: Levoleucovorin
         Generic Name: Levoleucovorin
      5. Brand Name: Cimzia
         Generic Name: Certolizumab Pegol
  b. Patient groups
    i. Osteoarthritis
    ii. Rheumatoid Arthritis
    iii. Juvenile Rheumatoid Arthritis
    iv. Ankylosing Spondylitis
  c. Indications
    i. Efficacy (system and algorithm address when compliance pattern is not adequate to maintain intended efficacy)
    ii. Safety (system and algorithm address when compliance pattern is problematic)
      1. Cardiovascular Thrombotic Events-Clinical trials of several COX-2 selective and nonselective NSAIDs of up to three years duration have shown an increased risk of serious cardiovascular (CV) thrombotic events, myocardial infarction, and stroke, which can be fatal 21) Post surgery (Surgery)
  a. Medications (Anti-coagulants, Antibiotics, Antifungal, Diuretics, Antacids, Antidepressant, Barbiturate, Benzodiazepine, Analgesic, Pain Relief)
  b. Patient groups (Vascular, Transplantation, Thoracic, Orthopedic, Oncology, Cardiac)
  c. Indications
    i. Efficacy (system and algorithm address when compliance pattern is not adequate to maintain intended efficacy)
    Safety (system and algorithm address when compliance pattern is problematic)

22) Geriatric (Geriatric, Family Practice, General Practice,)
  a. Medications
    i. Combinations of most commonly co-prescribed meds
  b. Patient groups (Heart failure, Syncope, Chronic seizures or epilepsy, Delirium, Dementia and cognitive impairment, Parkinson's disease, Insomnia, Chronic constipation, Chronic kidney disease)
  c. Indications
    i. Efficacy (system and algorithm address when compliance pattern is not adequate to maintain intended efficacy)
    ii. Safety (system and algorithm address when compliance pattern is problematic)

23) Obesity (Endocrine and Metabolism, Pediatrics, General Medicine, Psychiatry)
  a. Medications
    i. Oral meds for obesity (Orlistat (Xenical), Topiragen, diethylpropion, sibutramine, phendimetrazine)
  b. Patient groups (Overweight, Obese)
  c. Indications
    i. Efficacy (system and algorithm address when compliance pattern is not adequate to maintain intended efficacy)
    ii. Safety (system and algorithm address when compliance pattern is problematic)

24) Alzheimer (Geriatric, Family Practice, Psychiatry)
  a. Medications
    i. ARICEPT® (donepezil hydrochloride)
    ii. Namenda (memantine hydrochloride)
  b. Patient groups
    i. Mild to Moderate Alzheimer's Disease
    ii. Severe Alzheimer's Disease c. Indications
   i. Efficacy (system and algorithm address when compliance pattern is not adequate to maintain intended efficacy)
      1. The recommended starting dose of Namenda is 5 mg once daily. The recommended target dose is 20 mg/day. The dose should be increased in 5 mg increments to 10 mg/day (5 mg twice a day), 15 mg/day (5 mg and 10 mg as separate doses), and 20 mg/day (10 mg twice a day). The minimum recommended interval between dose increases is one week.
   ii. Safety (system and algorithm address when compliance pattern is problematic)
      1. Cardiovascular Conditions: Because of their pharmacological action, cholinesterase inhibitors may have vagotonic effects on the sinoatrial and atrioventricular nodes. This effect may manifest as bradycardia or heart block in patients both with and without known underlying cardiac conduction abnormalities. Syncopal episodes have been reported in association with the use of ARICEPT®.

25) Combinations of meds (All Medical Specialties)
   a. Medications (any combinations in a regimen)
   b. Patient groups
   c. Indications
      i. Efficacy (system and algorithm address when compliance pattern is not adequate to maintain intended efficacy)
      ii. Safety (system and algorithm address when compliance pattern is problematic)

26) HIV (Infectious Disease)
   a. Medications
      i. five major classes of anti-retroviral medications:
         1. nucleoside reverse transcriptase inhibitors (NRTIs),
         2. non-nucleoside reverse transcriptase inhibitors (NNRTIs),
         3. protease inhibitors (PIs),
            a. Kaletra (lopinavir and ritonavir)
         4. entry inhibitors, and
         5. integrase inhibitors.
   b. Patient groups
      i. indicated in combination with other antiretroviral agents for the treatment of HIV-1 infection
      ii. 25% have co-morbid depression
   c. Indications
      i. Efficacy (system and algorithm address when compliance pattern is not adequate to maintain intended efficacy)
      ii. Safety (system and algorithm address when compliance pattern is problematic)

27) Lipid and Cholesterol lowering (Cardiovascular, Family Practice, Internal Medicine, Endocrine and Metabolism, General Practice, Hematology, Preventative Medicine)
   a. Medications
      i. Lipitor
      ii. ZOCOR (simvastatin)
      iii. CRESTOR (rosuvastatin calcium)
      iv. VYTORIN (ezetimibe/simvastatin)
      v. ZETIA (ezetimibe)
      vi. TRICOR® (fenofibrate)
      vii. Niaspan (niacin)
      viii. PRAVACHOL® (pravastatin sodium)
   b. Patient groups
      i. Reductions in Risk of CHD Mortality and Cardiovascular Events
      ii. Hyperlipidemia
      iii. Adolescent Patients with Heterozygous Familial Hypercholesterolemia (HeFH)
   c. Indications
      i. Efficacy (system and algorithm address when compliance pattern is not adequate to maintain intended efficacy)
      ii. Safety (system and algorithm address when compliance pattern is problematic)
         1. Myopathy/Rhabdomyolysis. As with other statins, the risk of myopathy/rhabdomyolysis is dose related 28) Pain therapies (Surgery, General Practice, Psychiatry, Family Practice, Rheumatology, Sports Medicine)
   a. Medications
      i. Hydrocodone/Acetaminophen
      ii. LORTAB® 2.5/500 (hydrocodone bitartrate and acetaminophen) Tablets
      iii. PERCOCET® (oxycodone and acetaminophen)
      iv. ULTRAM® (tramadol hydrochloride)
      v. Celebrex® (celecoxib)
      vi. DARVOCET-N® 50 and DARVOCET-N® 100 (propoxyphene napsylate and acetaminophen)
      vii. MOTRIN® (ibuprofen)
      viii. LYRICA (pregabalin)
      ix. OXYCONTIN® (oxycodone hydrochloride)
      x. AMRIX® (cyclobenzaprine hydrochloride) for relief of muscle spasm associated with acute, painful musculoskeletal conditions
      xi. SOMA (carisoprodol) is indicated for the relief of discomfort associated with acute, painful musculoskeletal conditions in adults
   b. Patient groups
      i. for the relief of moderate to moderately severe pain.
      ii. Management of neuropathic pain associated with diabetic peripheral neuropathy
      iii. Management of post therapeutic neuralgia
      iv. Adjunctive therapy for adult patients with partial onset seizures
      v. Management of fibromyalgia
   c. Indications
      i. Efficacy (system and algorithm address when compliance pattern is not adequate to maintain intended efficacy)
         1. Good pain management practice dictates that the dose be individualized according to patient need using the lowest beneficial dose
      ii. Safety (system and algorithm address when compliance pattern is problematic)
         1. Drug Abuse and Dependence
         2. Respiratory Depression
         3. Acute Abdominal Conditions
         4. hepatic necrosis
         5. accidental and intentional overdose with propoxyphene products either alone or in combination with other CNS depressants, including alcohol
         6. useful to gradually discontinue the Darvocet-N over time to prevent the development of an opioid abstinence syndrome (narcotic withdrawal).
         7. Withdrawal of Antiepileptic Drugs (AEDs)
         8. As with all AEDs, withdraw LYRICA gradually to minimize the potential of increased seizure frequency in patients with seizure disorders. If LYRICA is discontinued, taper the drug gradually over a minimum of 1 week 29) Gastroesophageal Reflux Disease (GERD), Duodenal Ulcer and H. Pylori (Gastroenterology, Internal Medicine, General Practice, Family Practice)
   a. Medications
      i. Nexium (esomeprazole magnesium)
      ii. PREVACID (lansoprazole)
      iii. PRILOSEC (omeprazole)
      iv. PROTONIX (pantoprazole sodium)
      v. ACIPHEX® (rabeprazole sodium)
      vi. ZANTAC® 150 (ranitidine hydrochloride)
   b. Patient groups
      i. Healing of Erosive Esophagitis
      ii. Maintenance of Healing of Erosive Esophagitis Thaerapy up to 6 months
      iii. Symptomatic Gastroesophageal Reflux Disease
      iv. Risk Reduction of NSAID-Associated Gastric Ulcer
   c. Indications
      i. Efficacy (system and algorithm address when compliance pattern is not adequate to maintain intended efficacy)
         1. Treatment for 4-8 weeks
      ii. Safety (system and algorithm address when compliance pattern is problematic) Atrophic Gastritis
         1. Atrophic gastritis has been noted occasionally in gastric corpus biopsies from patients treated long-term with omeprazole, of which esomeprazole is an enantiomer.
         2. Combination Use of PRILOSEC with Arnoxicillin-Serious and occasionally fatal hypersensitivity (anaphylactic) reactions have been reported in patients on penicillin therapy
         3. daily treatment with any acid-suppressing medications over a long period of time (e.g., longer than 3 years) may lead to malabsorption of cyanocobalamin (Vitamin B-12)

30) Asthma (Pulmonary, Otorhinolaryngology, Pediatrics, General Practice, Family Practice)
   a. Medications
      i. SINGULAIR® (montelukast sodium)
      ii. ADVAIR DISKUS 100/50 (fluticasone propionate 100 mcg and salmeterol 50 mcg)
      iii. PROAIR HFA (albuterol sulfate) Inhalation Aerosol
      iv. PROVENTIL® HFA (albuterol sulfate)
      v. Combivent® (ipratropium bromide and albuterol sulfate) Inhalation Aerosol
      vi. Flovent® HFA 44 mcg (fluticasone propionate)
      vii. Long-term control asthma medications include:
         1. Corticosteroids (The inhaled form is the anti-inflammatory drug of choice for persistent asthma.)
         2. Mast cell stabilizers (anti-inflammatory drugs)
         3. Long acting beta-agonists (bronchodilators often used along with an anti-inflammatory drug)
         4. Theophylline (a bronchodilator used along with an anti-inflammatory drug to prevent nighttime symptoms)
         5. Leukotriene modifiers (an alternative to steroids and mast cell stabilizers)
         6. Xolair (an injectable asthma medication
   b. Patient groups
      i. Asthma
      ii. allergic rhinitis
      iii. prevention of exercise-induced bronchoconstriction
   c. Indications
      i. Efficacy (system and algorithm address when compliance pattern is not adequate to maintain intended efficacy)
      ii. Safety (system and algorithm address when compliance pattern is problematic)
         1. Do Not Exceed Recommended Dose: Fatalities have been reported in association with excessive use of inhaled sympathomimetic drugs in patients with asthma 31) Rhinitis and allergy (Pulmonary, Pediatrics, Otorhinolaryngology, General Practice, Family Practice)
   a. Medications
      i. ALLEGRA® (fexofenadine hydrochloride)
      ii. FLONASE® (fluticasone propionate) Nasal Spray
   b. Patient groups
      i. Seasonal Allergic Rhinitis
      ii. Chronic Idiopathic Urticaria
   c. Indications
      i. Efficacy (system and algorithm address when compliance pattern is not adequate to maintain intended efficacy)
      ii. Safety (system and algorithm address when compliance pattern is problematic)

32) BPH (prostrate) (Urology, Geriatric, Nephrology, Gastroenterology)
   a. Medications
      i. Flomax® (tamsulosin hydrochloride)
   b. Patient groups
      i. treatment of the signs and symptoms of benign prostatic hyperplasia (BPH)
   c. Indications
      i. Efficacy (system and algorithm address when compliance pattern is not adequate to maintain intended efficacy)
      ii. Safety (system and algorithm address when compliance pattern is problematic)
         1. symptomatic postural hypotension 33) ADHD (Psychiatry, Pediatrics, Family Practice, General Practice)
   a. Medications
      i. CONCERTA® (methylphenidate HCl)
   b. Patient groups
      i. treatment of Attention Deficit Hyperactivity Disorder (ADHD) in children 6 years of age and older, adolescents, and adults up to the age of 65
   c. Indications
      i. Efficacy (system and algorithm address when compliance pattern is not adequate to maintain intended efficacy)
         1. CONCERTA® Recommended Starting Doses and Dose Ranges
            a. Children 6-12 years of age 18 mg/day 18 mg-54 mg/day
            b. Adolescents 13-17 years of age 18 mg/day 18 mg-72 mg/day not to exceed 2 mg/kg/day
            c. Adults 18-65 years of age 18 or 36 mg/day 18 mg-72 mg/day
         2. Safety (system and algorithm address when compliance pattern is problematic)
            a. Drug Dependence
            b. Hypersensitivity to Methylphenidate
            c. Agitation
            d. Glaucoma e. Tics
  f. Serious Cardiovascular Events
  g. Psychiatric Adverse Events
  h. Seizures
  i. Long-Term Suppression of Growth
  j. Visual Disturbance
34) Ophthalmic eye drops (Ophthalmology, General Practice)
  a. Medications
    i. Xalatan® (latanoprost ophthalmic)
  b. Patient groups
    i. the reduction of elevated intraocular pressure in patients with open-angle glaucoma or ocular hypertension
  c. Indications
    i. Efficacy (system and algorithm address when compliance pattern is not adequate to maintain intended efficacy)
    ii. Safety (system and algorithm address when compliance pattern is problematic)
35) Overactive bladder (Urology, Nephrology, Family Practice, OB/GYN, Geriatric)
  a. Medications
    i. Detrol® LA (tolterodine tartrate)
  b. Patient groups
    i. the treatment of overactive bladder with symptoms of urge urinary incontinence, urgency, and frequency
  c. Indications
    i. Efficacy (system and algorithm address when compliance pattern is not adequate to maintain intended efficacy)
    ii. Safety (system and algorithm address when compliance pattern is problematic)
36) Gout (Rheumatology, General Practice, Family Practice, Geriatric, Endocrine and Metabolism)
  a. Medications
    i. ZYLOPRIM® (allopurinol)
  b. Patient groups
    i. the management of patients with signs and symptoms of primary or secondary gout
  c. Indications
    i. Efficacy (system and algorithm address when compliance pattern is not adequate to maintain intended efficacy)
      1. use should be individualized for each patient and requires an understanding of its mode of action and pharma-cokinetics
    ii. Safety (system and algorithm address when compliance pattern is problematic)
37) Erectile dysfunction (Urology, Family Practice, General Practice, Internal Medicine, Geriatric)
  a. Medications
    i. CIALIS® (tadalafil)
    ii. VIAGRA® (sildenafil citrate)
  b. Patient groups
  c. Indications
    i. Efficacy (system and algorithm address when compliance pattern is not adequate to maintain intended efficacy)
    ii. Safety (system and algorithm address when compliance pattern is problematic)
      1. Cardiovascular
      2. Potential for Drug Interactions
      3. Prolonged Erection
      4. Eye non-arteritic anterior ischemic optic neuropathy (NAION),
      5. Sudden Hearing Loss
38) Vitamins (General Practice, Family Practice, all specialties)
  a. Medications
    i. Folic acid
    ii. Vitamin D:
      1. Alfacalcidol: 1-alpha-hydroxycholecalciferol, 1 alpha (OH)D3.
      2. Calcifediol: 25-HCC, 25-hydroxycholecalciferol, 25-hydroxyvitamin D3, 25-OHCC, 25-OHD3.
      3. Calcipotriene: Calcipotriol.
      4. Calcitriol: 1,25-DHCC, 1,25-dihydroxycholecalciferol, 1,25-dihydroxyvitamin D3, 1,25-di-OHC, 1,25(OH)2D3.
      5. Cholecalciferol: Activated 7-dehydrocholesterol, colecalciferol, Vitamin D3.
      6. Dihydrotachysterol: DHT, dihydrotachysterol 2, dichysterol.
      7. Ergocalciferol: Activated ergosterol, Calciferol, Ergocalciferolum, Irradiated ergosterol, Viosterol, Vitamin D2.
      8. Paricalcitol: 19-nor-1,25-dihydroxyvitamin D2, Paracalcin.
    iii. Other (Vitamin A, B1, B2, B3, B5, B6, B7, B9, B12, C, D, E, K)
  b. Patient groups (all)
  c. Indications
    i. Efficacy (system and algorithm address when compliance pattern is not adequate to maintain intended efficacy)
    ii. Safety (system and algorithm address when compliance pattern is problematic)
39) Osteoporosis (Geriatrics, Family Practice, OB/Gyn, Endocrine and Metabolism)
  a. Medications
    i. BONIVA® (ibandronate sodium)
    ii. EVISTA (raloxifene hydrochloride)
  b. Patient groups
    i. Treatment and Prevention of Postmenopausal Osteoporosis
  c. Indications
    i. Efficacy (system and algorithm address when compliance pattern is not adequate to maintain intended efficacy)
    ii. Safety (system and algorithm address when compliance pattern is problematic)
      1. Upper Gastrointestinal Adverse Reactions
      2. In clinical trials, EVISTA-treated women had an increased risk of venous thromboembolism (deep vein thrombosis and pulmonary embolism).
      3. increased risk of death due to stroke
40) Smoking cessation (Psychiatry)
  a. Medications
    i. CHANTIX® (varenicline)
  b. Patient groups (Smoker)
  c. Indications
    i. Efficacy (system and algorithm address when compliance pattern is not adequate to maintain intended efficacy)
      1. recommended dose of CHANTIX is 1 mg twice daily following a 1-week titration as follows:
        a. Days 1 — 3:0.5 mg once daily
        b. Days 4 — 7:0.5 mg twice daily
        c. Day 8 — End of treatment: 1 mg twice daily ii. Safety (system and algorithm address when compliance pattern is problematic)
1. Neuropsychiatric Symptoms and Suicidality
41) Migraine (Neurology, Family Practice, General Practice, Psychiatry)
   a. Medications
      i. IMITREX® (sumatriptan succinate)
      ii. Depakote ER (divalproex sodium)
   b. Patient groups
      i. for the acute treatment of migraine attacks with or without aura in adults
   c. Indications
      i. Efficacy (system and algorithm address when compliance pattern is not adequate to maintain intended efficacy)
      ii. Safety (system and algorithm address when compliance pattern is problematic)
         1. Risk of Myocardial Ischernia and/or Infarction and Other Adverse Cardiac Events: Sumatriptan should not be given to patients with documented ischemic or vasospastic coronary artery disease (CAD)
42) Angina (Cardiology, Family Practice, General Practice, Geriatric)
   a. Medications
      i. ISMO (isosorbide mononitrate)
      ii. COVERA-HS® (verapamil hydrochloride)
   b. Patient groups
      i. prevention of angina pectoris due to coronary artery disease
   c. Indications
      i. Efficacy (system and algorithm address when compliance pattern is not adequate to maintain intended efficacy)
      ii. Safety (system and algorithm address when compliance pattern is problematic)
43) Alcoholism (Psychiatry, Family Practice, General Practice)
   a. Medications
      i. Antabuse
   b. Patient groups (alcoholic)
   c. Indications
      i. Efficacy (system and algorithm address when compliance pattern is not adequate to maintain intended efficacy)
      ii. Safety (system and algorithm address when compliance pattern is problematic)

As a simple example, a treatment regimen may be input to a processor, defined as taking two tablets per day, at 12 hour intervals—i.e., one tablet at 8:00 a.m. and one tablet at 8:00 p.m. The input regimen would include a window for each dose, such as plus or minus 30 minutes. The usage data from a monitor would show when each tablet was taken, for example by noting the time of opening of a single-tablet compartment in the monitor. The usage data could be communicated in real time, or stored and communicated in batches, to a compliance pattern processor. The compliance pattern processor could identify a pattern over time, e.g., one month, of, for example, timely, near-miss (e.g., within 30 minutes on one side of the window), distant-miss (e.g., between 30 minutes and two hours on one side of the window), and complete-miss doses. Preferably, the compliance pattern processor would also identify patterns of misses before the window and/or patterns of misses after the window. A treatment regimen processor would receive the compliance pattern. It would optionally also contain previously-stored patient history, medication properties, and other data, and could also continue to receive such data, and correlate it to associated compliance patterns. Upon correlating a new compliance pattern to outcome data, for example, a pattern of increasingly distant misses and complete misses of the evening window but not of the morning window, to reduced efficacy of the tablets, it could generate an adjusted treatment regimen of one larger-dose, controlled release tablet to be taken only during the morning window. Outcomes data associated with this new treatment regimen could be input by, e.g., the patient's healthcare provider or by a diagnostic tool packaged with or part of a medication monitor, preferably tailored to a medication packaged with the monitor. The biomarker device 440 illustrated in FIG. 4 is one example of such a diagnostic tool. The diagnostic tool packaged with the medication monitor may be, for example, a patch, a weight scale, a blood pressure monitor or a microchip-containing device that is configured to be inserted into, for example, a mobile device. Thus, the correlations available to the treatment regimen processor grow over time to improve the usefulness of the system.

While methods, systems, and apparatus for patient medication regimen compliance monitoring, medication regimen establishment and adjustment, medication usage and outcomes data presentation, compliance pattern presentation and usage, etc. have been described in relationship to exemplary embodiments, it is evident that many alternatives, modifications, and variations would be apparent to those skilled in the art. Accordingly, embodiments of the methods and systems as set forth herein are intended to be illustrative, not limiting. There are changes that may be made without departing from the spirit and scope of the exemplary embodiments.

It will be appreciated that the above-disclosed and other features and functions, or alternatives thereof, may be desirably combined into many other different systems or applications. Also, various alternatives, modifications, variations, or improvements therein may be subsequently made by those skilled in the art without departing from the scope of the invention.

What is claimed is:

1. A method of optimizing treatment of a medication recipient patient, comprising:
   administering at least one active medication to the patient as a part of a medication treatment regimen;
   providing the patient with a reprogrammable medication monitor capable of providing usage data regarding the patient's compliance with the medication treatment regimen, the medication treatment regimen being established based on a medication compliance pattern of the patient, wherein the compliance pattern is a statistical pattern derived from a plurality of data points gathered over a period of time of not less than one week, where the data points include doses missed, doses taken early, doses taken late, and taken on time, the medication monitor including:
      a housing body that includes a housing for containing medication or medication packaging, the housing body defining an opening to accommodate insertion and removal of the medication or of the medication packaging, and
      a removal sensor that senses at least one of (i) removal of the medication or of the medication packaging and (ii) opening of the housing body;
   collecting the usage data from the medication monitor at a central server over a predetermined period of time;
   determining safety and efficacy of the medication treatment regimen;

determining the patient's pattern of compliance with the medication treatment regimen based on the usage data collected from the medication monitor;

obtaining diagnostic test results from a biomarker device, the diagnostic test results being indicative of a response of the patient to the medication treatment regimen over the predetermined period of time, the biomarker device being configured to be implanted in the patient or provided external to the patient;

correlating the patient's pattern of compliance and the patient's diagnostic test results with patterns of compliance and diagnostic test results from a population of patients to obtain a correlation;

outputting at least one recommendation based on the correlation and based on the safety and efficacy of the medication treatment regimen, the at least one recommendation selected from the group consisting of:

changing at least one dosage of at least one active medication used in the medication treatment regimen, changing a timing of recommended usage of at least one active medication used in the medication treatment regimen, and replacing the at least one active medication used in the medication treatment regimen with at least one different medication; and adjusting and administering the medication treatment regimen of the patient based on the at least one recommendation.

2. The method of claim 1, wherein the biomarker device is implanted in the patient so as to obtain the diagnostic test results, and the biomarker device includes a wireless transmitter that outputs the diagnostic test results.

3. The method of claim 1, wherein the biomarker device is a device that is external to the patient, and the biomarker device is one of a weight scale, a blood pressure monitor, a patch provided on skin of the patient, and a detection device that can be inserted into a mobile transmitter device.

4. The method of claim 1, wherein the biomarker device communicates wirelessly to the medication monitor.

5. The method of claim 1, wherein the patient's diagnostic test results are provided to the central server.

6. The method of claim 4, wherein the patient's diagnostic test results are provided to the central server by the medication monitor.

7. The method of claim 1, wherein the patient's diagnostic test results include a concentration of the at least one active medication in the patient's blood during the predetermined period of time.

8. The method of claim 1, wherein the patient's diagnostic test results include results indicative of the efficacy of the treatment regimen.

9. The method of claim 1, wherein the patient's diagnostic test results include results of detecting presence or absence of a biomarker of malignancy or infection.

10. The method of claim 1, wherein the patient's diagnostic test results include results of detecting presence or absence of a marker for adverse effects.

11. The method of claim 1, wherein the patient's diagnostic test results include results indicative of a level of immunosuppression of the patient to the treatment regimen over the predetermined period of time.

12. The method of claim 1, wherein the patient's pattern of compliance and the patient's diagnostic test results are correlated with patterns of compliance and diagnostic test results from patients of the population that experienced reduced efficacy such that the correlation is indicative of the patient experiencing reduced efficacy of the medication treatment regimen, which can be ameliorated by adjusting the medication treatment regimen of the patient based on the at least one recommendation.

13. The method of claim 1, wherein the patient's pattern of compliance and the patient's diagnostic test results are correlated with patterns of compliance and diagnostic test results from patients of the population that had an adverse effect such that the correlation is indicative of the patient developing an adverse effect, which can be ameliorated by adjusting the medication treatment regimen of the patient based on the at least one recommendation.

14. The method of claim 1, wherein the patient's pattern of compliance and the patient's diagnostic test results are correlated with patterns of compliance and diagnostic test results from patients of the population who had an infection or a malignancy such that the correlation is indicative of the patient developing an infection or a malignancy, and the infection or the malignancy can be ameliorated by adjusting the medication treatment regimen of the patient based on the at least one recommendation.

* * * * *